US012765799B1

(12) United States Patent
Nyberg et al.

(10) Patent No.: US 12,765,799 B1
(45) Date of Patent: Oct. 20, 2026

(54) BREATH PATH CONFIGURATION FOR AN ALCOHOL DETECTION DEVICE

(71) Applicant: Consumer Safety Technology, LLC, Des Moines, IA (US)

(72) Inventors: Stephen R. Nyberg, Kansas City, MO (US); Nicholas Greusel, Overland Park, KS (US); Eric Robert Hoofman, Merriam, KS (US)

(73) Assignee: Consumer Safety Technology, LLC, Urbandale, IA (US)

(*) Notice: Subject to any disclaimer, the term of this patent is extended or adjusted under 35 U.S.C. 154(b) by 352 days.

(21) Appl. No.: 18/240,118

(22) Filed: Aug. 30, 2023

Related U.S. Application Data

(60) Provisional application No. 63/402,760, filed on Aug. 31, 2022.

(51) Int. Cl.

| | |
|---|---|
| ***A61B 5/08*** | (2006.01) |
| ***A61B 5/00*** | (2006.01) |
| ***A61B 5/087*** | (2006.01) |
| ***A61B 5/097*** | (2006.01) |
| ***A61B 10/00*** | (2006.01) |

(52) U.S. Cl.
CPC .............. *A61B 5/082* (2013.01); *A61B 5/087* (2013.01); *A61B 5/097* (2013.01); *A61B 5/4845* (2013.01); *A61B 2010/0087* (2013.01)

(58) Field of Classification Search
CPC ......... A61B 5/082; A61B 5/087; A61B 5/097; A61B 5/4845; A61B 2010/0087
USPC ............. 600/529, 532, 538, 543; 422/83, 84
See application file for complete search history.

(56) References Cited

U.S. PATENT DOCUMENTS

| | | | | |
|---|---|---|---|---|
| 3,818,899 A | | 6/1974 | Venema | |
| 4,292,978 A | | 10/1981 | Guth | |
| 4,297,871 A | | 11/1981 | Wright et al. | |
| 4,332,771 A | | 6/1982 | Leichnitz | |
| 4,407,152 A | | 10/1983 | Guth et al. | |
| 4,592,443 A | | 6/1986 | Simon | |
| 5,426,415 A | | 6/1995 | Prachar et al. | |
| 5,465,728 A | * | 11/1995 | Phillips | A61B 5/097 128/204.17 |
| 5,759,368 A | | 6/1998 | Kuehn | |
| 5,929,319 A | | 7/1999 | King et al. | |

(Continued)

FOREIGN PATENT DOCUMENTS

| | | |
|---|---|---|
| AU | 1988010970 | 4/1988 |
| EP | 0327396 | 10/1990 |

(Continued)

*Primary Examiner* — Puya Agahi
(74) *Attorney, Agent, or Firm* — Pauly, DeVries Smith & Deffner LLC

(57) ABSTRACT

Embodiments herein relate to breath alcohol detection devices. In an embodiment, a breath alcohol detection device is included having a breath path. The breath path is included having a breath path inlet, a breath path outlet, a first bend disposed between the breath path inlet and the breath path outlet, a second bend disposed between the first bend and the breath path outlet, and an elongate portion disposed between the second bend and the breath path outlet. The breath alcohol detection device can include a breath path heater, wherein the breath path heater is configured to wrap around an outside portion of the breath path. Other embodiments are also included herein.

7 Claims, 15 Drawing Sheets

(56) References Cited

U.S. PATENT DOCUMENTS

| | | | |
|---|---|---|---|
| 6,150,177 | A | 11/2000 | Stock |
| 6,792,793 | B2 | 9/2004 | Mendoza et al. |
| 7,095,501 | B2 | 8/2006 | Lambert et al. |
| 7,204,335 | B2 | 4/2007 | Stewart et al. |
| 7,329,390 | B2 | 2/2008 | Chrzan et al. |
| 7,736,903 | B2 | 6/2010 | Lambert et al. |
| 7,993,281 | B2 | 8/2011 | Stock et al. |
| 8,822,929 | B2 | 9/2014 | Nesa et al. |
| 9,089,279 | B2 | 7/2015 | Wang et al. |
| 9,316,614 | B2 | 4/2016 | Stock et al. |
| 9,329,167 | B2 | 5/2016 | Son |
| 9,366,665 | B1 | 6/2016 | Granstam et al. |
| 9,465,004 | B2 | 10/2016 | Fix et al. |
| 9,481,245 | B2 | 11/2016 | Nelson et al. |
| 9,696,294 | B2 | 7/2017 | Phillips |
| 10,031,072 | B2 | 7/2018 | Nesa et al. |
| 10,130,284 | B2 | 11/2018 | Johnson |
| 10,178,963 | B1 | 1/2019 | Azimi et al. |
| 10,343,170 | B2 | 7/2019 | Ahmad et al. |
| 10,359,417 | B2 | 7/2019 | Hammarlund et al. |
| 10,898,108 | B2 | 1/2021 | Stambeck |
| 2004/0045889 | A1 | 3/2004 | Harkonen et al. |
| 2010/0043524 | A1 | 2/2010 | Takata |
| 2011/0266160 | A1 | 11/2011 | Campbell et al. |
| 2013/0169442 | A1 | 7/2013 | Ruocco et al. |
| 2013/0305808 | A1 | 11/2013 | Yoo |
| 2014/0288454 | A1* | 9/2014 | Paz .................... G01N 33/497 600/532 |
| 2015/0008063 | A1 | 1/2015 | Walter et al. |
| 2015/0197151 | A1 | 7/2015 | Ballard |
| 2016/0086021 | A1 | 3/2016 | Grohman et al. |
| 2019/0274584 | A1 | 9/2019 | Davis et al. |
| 2021/0007185 | A1 | 1/2021 | Jang et al. |
| 2021/0022673 | A1 | 1/2021 | Verbeck et al. |
| 2021/0177303 | A1* | 6/2021 | Pimentel ................ A61B 5/742 |

FOREIGN PATENT DOCUMENTS

| | | |
|---|---|---|
| EP | 2544000 | 8/2016 |
| WO | 9222813 | 12/1992 |
| WO | 2010025478 | 3/2011 |
| WO | 2013191633 | 12/2013 |
| WO | 2020260687 | 12/2020 |
| WO | 2021254760 | 12/2021 |

* cited by examiner

BREATH PATH CONFIGURATION FOR AN ALCOHOL DETECTION DEVICE

This application claims the benefit of U.S. Provisional Application No. 63/402,760, filed Aug. 31, 2022, the content of which is incorporated herein by reference in its entirety.

FIELD

Embodiments herein relate generally to breath alcohol detection devices, and more specifically to breath path configurations for breath alcohol detection devices.

BACKGROUND

Breath alcohol detection devices are used to measure an amount of alcohol in a user's breath. It is known that concentration of alcohol in a user's breath is closely proportional to the concentration of alcohol in the user's blood, which is typically the basis upon which intoxication is legally determined. Generally, a user blows into a mouthpiece of an alcohol detection device and a breath path is configured to transport at least a portion of the breath sample to an alcohol-sensing element of the alcohol detection device.

SUMMARY

In a first aspect, a breath alcohol detection device can be included having a breath path. The breath path can be included having a breath path inlet, a breath path outlet, a first bend disposed between the breath path inlet and the breath path outlet, a second bend disposed between the first bend and the breath path outlet, and an elongate portion disposed between the second bend and the breath path outlet. The breath alcohol detection device can further include a breath path heater, wherein the breath path heater can be configured to wrap around an outside portion of the breath path.

In a second aspect, in addition to one or more of the preceding or following aspects, or in the alternative to some aspects, the breath path heater can include a plurality of breath path heater contact pads.

In a third aspect, in addition to one or more of the preceding or following aspects, or in the alternative to some aspects, the breath path can be configured to fit within a housing of the breath alcohol detection device. The housing includes a first circuit board, wherein plurality of breath path heater contact pads can be configured to receive power from a plurality of spring contacts disposed on the first circuit board.

In a fourth aspect, in addition to one or more of the preceding or following aspects, or in the alternative to some aspects, the breath path heater can include a temperature sensor configured to measure a temperature of the breath path.

In a fifth aspect, in addition to one or more of the preceding or following aspects, or in the alternative to some aspects, the breath path heater can include a first heater portion that can include a first resistive heating element, a second heater portion that can include a second resistive heating element, and a connecting portion joining the first heater portion and second heater portion.

In a sixth aspect, in addition to one or more of the preceding or following aspects, or in the alternative to some aspects, the connecting portion does not include a heating element.

In a seventh aspect, in addition to one or more of the preceding or following aspects, or in the alternative to some aspects, the first heater resistive heating element and second heater resistive heating element can be in series and can be controlled together. In an eighth aspect, in addition to one or more of the preceding or following aspects, or in the alternative to some aspects, the first heater resistive heating element and second heater resistive heating element can be controlled independently.

In a ninth aspect, in addition to one or more of the preceding or following aspects, or in the alternative to some aspects, the breath path heater includes a flexible circuit board.

In a tenth aspect, in addition to one or more of the preceding or following aspects, or in the alternative to some aspects, the first bend can have a first bend angle of at least about 80 degrees and at most about 90 degrees, wherein the first bend angle can be measured between a longitudinal axis of the breath path inlet and a longitudinal axis of a first downstream portion.

In an eleventh aspect, in addition to one or more of the preceding or following aspects, or in the alternative to some aspects, wherein breath path includes an inlet portion extending longitudinally from the breath path inlet to an inlet portion end, wherein the first downstream portion extends from the inlet portion end toward the second bend.

In a twelfth aspect, in addition to one or more of the preceding or following aspects, or in the alternative to some aspects, the second bend can have a second bend angle of at least about 170 degrees and at most about 190 degrees.

In a thirteenth aspect, in addition to one or more of the preceding or following aspects, or in the alternative to some aspects, the breath path further includes an inlet portion and a first downstream portion extending between the inlet portion and the second bend, wherein the second bend angle can be measured between the first portion of the elongate portion and the first downstream portion.

In a fourteenth aspect, in addition to one or more of the preceding or following aspects, or in the alternative to some aspects, further can include a breath alcohol sensor in fluid communication with the breath path space.

In a fifteenth aspect, in addition to one or more of the preceding or following aspects, or in the alternative to some aspects, the breath alcohol sensor further can include a breath alcohol sensor housing having a first breath alcohol sensor port and a second breath alcohol sensor port, wherein the first breath alcohol sensor port and the second breath alcohol sensor port can be in fluid communication with the breath path space.

In a sixteenth aspect, in addition to one or more of the preceding or following aspects, or in the alternative to some aspects, the first breath path port can be configured to interface with the first breath alcohol sensor port and the second breath path port can be configured to interface with the second breath alcohol sensor port.

In a seventeenth aspect, in addition to one or more of the preceding or following aspects, or in the alternative to some aspects, the first and second breath alcohol sensor ports can be sized to fit within and form a seal with the first and second breath path ports.

In an eighteenth aspect, in addition to one or more of the preceding or following aspects, or in the alternative to some aspects, the first and second breath alcohol sensor ports and the first and second breath path ports can be substantially conical in profile.

In a nineteenth aspect, in addition to one or more of the preceding or following aspects, or in the alternative to some aspects, the first breath path port can be in fluid communication with the first pressure sensor through the first breath alcohol sensor port and a bypass path in the breath alcohol sensor housing.

In a twentieth aspect, in addition to one or more of the preceding or following aspects, or in the alternative to some aspects, the second breath path port can be in fluid communication with the second pressure sensor through the second breath alcohol sensor port and the breath alcohol sensor.

In a twenty-first aspect, in addition to one or more of the preceding or following aspects, or in the alternative to some aspects, further can include an anti-circumvention sensor assembly. The anti-circumvention sensor assembly can include at least one of or both of a temperature sensor and a humidity sensor, wherein the anti-circumvention sensor assembly can be disposed at the breath path outlet. The anti-circumvention sensor assembly can be configured to measure a temperature of the breath sample, a humidity of the breath sample, or both a temperature and a humidity of the breath sample.

In a twenty-second aspect, in addition to one or more of the preceding or following aspects, or in the alternative to some aspects, the anti-circumvention sensor can be located outside of the breath path.

In a twenty-third aspect, in addition to one or more of the preceding or following aspects, or in the alternative to some aspects, the breath path can be substantially rectangular in cross section.

In a twenty-fourth aspect, a method of replacing a first breath path in a breath alcohol detection device can be included. The method can include removing a top hatch from the breath alcohol detection device. The method can include pulling the first breath path out of the breath alcohol detection device, the first breath path having a first breath path inlet, a first breath path outlet, and a first breath path port, inserting a second breath path into the breath alcohol detection device, the second breath path having a second breath path inlet, a second breath path outlet, and a second breath path port. The method can include placing the top hatch on the breath alcohol detection device over the second breath path.

In a twenty-fifth aspect, in addition to one or more of the preceding or following aspects, or in the alternative to some aspects, wherein removing a top hatch from the breath alcohol detection device includes removing a threaded fastener from a first side of the top hatch and pivoting the top hatch about the first side.

In a twenty-sixth aspect, in addition to one or more of the preceding or following aspects, or in the alternative to some aspects, the breath alcohol detection device can include a breath alcohol sensor. The breath alcohol sensor can include a breath alcohol sensor housing having a first breath alcohol sensor port, wherein the first breath path port can be configured to interface with the first breath alcohol sensor port. Pulling the first breath path out of the breath alcohol detection device can include disengaging the first breath path port from the first breath alcohol sensor port.

In a twenty-seventh aspect, in addition to one or more of the preceding or following aspects, or in the alternative to some aspects, the second breath path port can be configured to interface with the first breath alcohol sensor port, and wherein inserting a second breath path into the breath alcohol detection device includes aligning the second breath path port with the first breath alcohol sensor port.

In a twenty-eighth aspect, in addition to one or more of the preceding or following aspects, or in the alternative to some aspects, the first and second breath alcohol sensor ports can be sized to fit within and form a seal with the first and second breath path ports, and wherein the first and second breath alcohol sensor ports and the first and second breath path ports can be substantially conical in profile.

In a twenty-ninth aspect, in addition to one or more of the preceding or following aspects, or in the alternative to some aspects, the first breath path includes a breath path heater removably attached to the first breath path. The breath alcohol detection device further can include a first circuit board, wherein pulling the first breath path out of the breath alcohol detection device includes disengaging plurality of breath path heater contact pads from a plurality of spring contacts disposed on the first circuit board.

In a thirtieth aspect, in addition to one or more of the preceding or following aspects, or in the alternative to some aspects, the method further can include, after pulling the first breath path out of the breath alcohol detection device, removing the first breath path heater from the first breath path.

In a thirty-first aspect, in addition to one or more of the preceding or following aspects, or in the alternative to some aspects, the second breath path includes a breath path heater removably attached to the second breath path, the method further can include, attaching the second breath path heater to the second breath path, and engaging a second plurality of breath path heater contact pads with the plurality of spring contacts disposed on the first circuit board.

In a thirty-second aspect, in addition to one or more of the preceding or following aspects, or in the alternative to some aspects, a first gasket can be disposed on the second inlet of the second breath path, wherein placing the top hatch on the breath alcohol detection device over the second breath path further includes compressing the first gasket with the top hatch.

In a thirty-third aspect, in addition to one or more of the preceding or following aspects, or in the alternative to some aspects, the second breath path includes a second gasket disposed on the second outlet, wherein placing the top hatch on the breath alcohol detection device over the second breath path further includes compressing the second gasket with an interior surface of one of a left-side housing wall portion or a right-side housing wall portion of the breath alcohol detection device.

In a thirty-fourth aspect, in addition to one or more of the preceding or following aspects, or in the alternative to some aspects, wherein pulling the first breath path out of the breath alcohol detection device includes pulling the breath path out through a top hatch opening of the breath alcohol detection device.

In a thirty-fifth aspect, in addition to one or more of the preceding or following aspects, or in the alternative to some aspects, the method can further include removing a mouthpiece from the breath alcohol detection device prior to removing the top hatch from the breath alcohol detection device.

In a thirty-sixth aspect, in addition to one or more of the preceding or following aspects, or in the alternative to some aspects, the second breath path further can include a protrusion disposed above the second breath path outlet, wherein placing the top hatch on the breath alcohol detection device over the second breath path includes applying pressure to the protrusion.

In a thirty-seventh aspect, in addition to one or more of the preceding or following aspects, or in the alternative to some aspects, the second breath path includes a gasket disposed on the second breath path outlet, wherein the gasket can be configured to wrap around the protrusion. Placing the top hatch on the breath alcohol detection device over the second breath path further includes squeezing the gasket against the protrusion.

In a thirty-eighth aspect, a breath alcohol detection device can be included having a housing. The housing can include a top hatch, a front housing, and a rear housing. The breath alcohol detection device can include a breath path disposed within the housing, the breath path defining a breath path space, the breath path can be included having a breath path inlet configured to align with a housing inlet, the breath path inlet configured to receive a breath sample, a breath path outlet configured to align with a housing outlet, an elongate portion disposed between the breath path inlet and the breath path outlet, wherein the elongate portion runs parallel to the top hatch of the housing. The breath alcohol detection device can include a temperature sensor disposed between the breath path outlet and the housing outlet, wherein the temperature sensor can be configured to measure a temperature of the breath sample.

In a thirty-ninth aspect, in addition to one or more of the preceding or following aspects, or in the alternative to some aspects, the breath path the breath alcohol detection device can further include a first bend disposed between the breath path inlet and the breath path outlet, and a second bend disposed between the first bend and the breath path outlet.

In a fortieth aspect, in addition to one or more of the preceding or following aspects, or in the alternative to some aspects, the elongate portion of the breath path the breath alcohol detection device can further include a first portion having a first cross-sectional area, a second portion having a second cross-sectional area, and a restriction portion disposed between the first portion and the second portion, the restriction portion having a third cross-sectional area, wherein the third cross-sectional area can be smaller than the first cross-sectional area and the second cross-sectional area.

In a forty-first aspect, in addition to one or more of the preceding or following aspects, or in the alternative to some aspects, the breath alcohol detection device can further include a first pressure sensor in fluid communication with the first portion through a first breath path port, the first pressure sensor configured to measure a first pressure value of the breath sample, and a second pressure sensor in fluid communication with the restriction portion through a second breath path port, the second pressure sensor, configured to measure a second pressure value of the breath sample.

In a forty-second aspect, in addition to one or more of the preceding or following aspects, or in the alternative to some aspects, further can include a breath alcohol sensor in fluid communication with the breath path space.

In a forty-third aspect, in addition to one or more of the preceding or following aspects, or in the alternative to some aspects, the breath alcohol sensor can include a fuel cell-type detector element.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
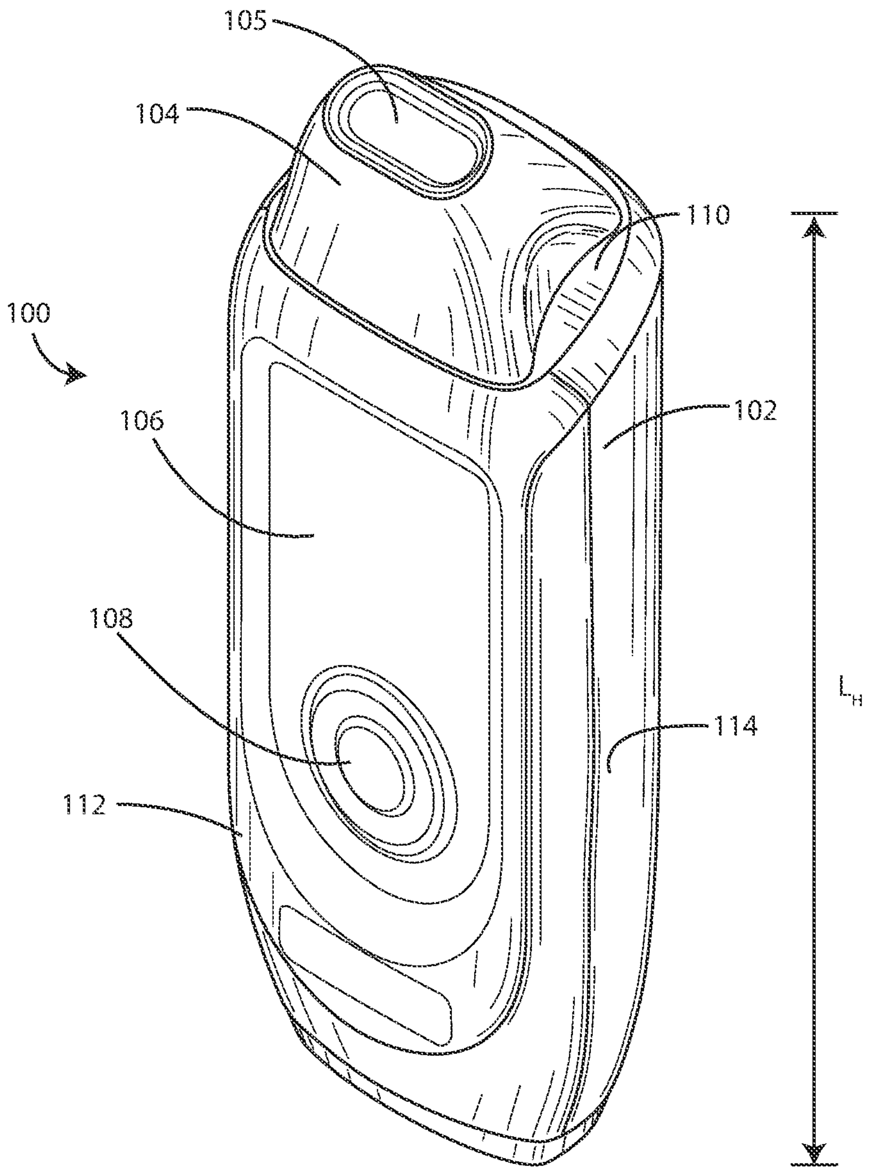
FIG. 1 is a perspective view of a breath alcohol detection device in accordance with various embodiments herein.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Embodiments herein relate to a breath path for a breath alcohol detection device. In some embodiments, a breath path heater is provided that contacts an outside surface of the breath path. In some embodiments, the breath alcohol detection device contains a breath path removably disposed within the breath alcohol detection device housing, so that a first breath path can be removed and replaced with a second breath path in an efficient manner, in which mechanical and electrical connections are made without requiring the use of a tool. In some embodiments, a breath sample may enter the breath path at a breath path inlet aligned with a housing inlet at the top, end, or side of the housing and at least a portion of the breath sample may exit the breath path through a breath path outlet aligned with a housing outlet, where the housing outlet has one or more openings in one or both of the left or right sides of the housing.

In various embodiments, the breath path defines a serpentine flow channel between the breath path inlet and the breath path outlet. The flow channel may have geometry that causes the air fluid stream to make a first bend of approximately 90 degrees followed by a second bend of approximately 180 degrees, and potentially subsequent bends as needed to homogenize the air mixture. The breath path further includes an elongated portion downstream from the second or subsequent bends. The elongated portion can include a first portion, a second portion, and a restriction portion disposed between the first portion and the second portion. The restriction portion has smaller cross-sectional area than the first and second portions. A first pressure value of the breath sample may be measured at the first portion of the breath path and a second pressure value of the breath sample may be measured at the restriction portion of the breath path. In addition, or alternatively, a third pressure value may be measured in the second portion. All or any one or any combination of two may be measured. By measuring the pressure difference at two different locations in the flow channel of the breath path, the flow rate of the breath sample may be derived.

The serpentine breath path has several benefits over an equivalent straight breath path. The serpentine breath path has the same effective length as a straight breath path while taking up less space in the alcohol detection device, thus leaving more room for other electrical components within the alcohol detection device housing or allowing the device to be a smaller size. The winding shape of the breath path also reduces the external surface area and overall mass of the breath path compared to a straight breath path having the same effective length, reducing the power requirement to heat the breath path. Finally, the serpentine breath path allows the breath sample to be delivered at the top center, edge, or end of the breath alcohol detection device and exhaust out of one of the sides of the breath alcohol detection device, perpendicular to the user, and away from the grip of the user. This is believed to reduce the chance of a user blocking the exhaust with their hands.

In various embodiments, the breath alcohol detection device includes an anti-circumvention sensor, such as a temperature sensor, humidity sensor, both, or other sensors that measure the characteristics of the breath mixture or how the breath moves through the breath path, disposed between a breath path outlet of the breath path and an outlet of the housing of the breath alcohol detection device. The anti-circumvention sensor may be configured to measure a quality of the breath sample, such as temperature or humidity. In various embodiments, the temperature sensor is outside of the breath path. In various embodiments, the temperature sensor is outside of a zone through which the breath path will be moved if it is removed and replaced, such as outside of a zone between the breath path and a hatch of the housing. As a result, the anti-circumvention sensor does not have to be removed, moved, or replaced in order to replace the breath path.

Referring now to FIG. 1, a perspective view of a breath alcohol detection device is shown in accordance with various embodiments herein. The breath alcohol detection device 100 can include a housing 102. The housing 102 is preferably a relatively hard durable material that serves to protect the internal components of the breath alcohol detection device 100. In various embodiments, the housing is formed from a top hatch 110 or access panel, a front housing 112, and a rear housing 114. The top hatch 110, front housing 112, and rear housing 114 may be formed by injection molding of hard plastic, or other similar materials or formed by other manufacturing methods. In various embodiments, top hatch 110, front housing 112, and rear housing 114 are joined together in a fashion that permits access to the internal components of the alcohol detection device 100 without destruction of the outer case. For example, threaded fasteners, friction and snap fits, or the like may be used to join the top hatch 110, front housing 112, and rear housing 114. In various embodiments, the breath alcohol detection device 100 is constructed to be of a suitable shape and size to be a handheld device, such that a user may pick the unit up to facilitate conducting a breath test.

The breath alcohol detection device 100 can include a mouthpiece 104 having a mouthpiece inlet 105 shaped to receive the mouth of a user providing a breath sample to the breath alcohol detection device. In various embodiments, the mouthpiece 104 is configured to be removably attachable to the breath alcohol detection device 100 by means of a friction or snap fit, or similar mechanism. This permits each driver to have their own mouthpiece 104 for sanitary reasons, and it also permits easy cleaning or replacement of the mouthpiece 104. In various embodiments, the mouthpiece can be formed from a substantially rigid material configured to retain its shape when a breath sample is provided to the breath alcohol detection device 100. Alternatively, the mouthpiece 104 is formed from a compliant material configured to conform to a user's mouth when a breath sample is provided to the breath alcohol detection device 100. The mouthpiece 104 can be made from any suitable material or materials including but not limited to plastics, rubbers, silicone, easily formable metals, or the like.

The breath alcohol detection device 100 may also include a display 106 configured to provide a visual interface for a user. The display 106 may be any suitable type of display such as a color liquid crystal display with back lighting. The display 106 may be used to show operating instructions, device status, and communications from a service provider.

The breath alcohol detection device 100 can further include a user input 108 to allow a user to operate and control the alcohol detection device 100. In various embodiments, the user input can include one or more buttons that can be dedicated to a specific purpose or may have "soft" functionality as dictated by the current operating needs of the system.

Breath Path

Figure 2:
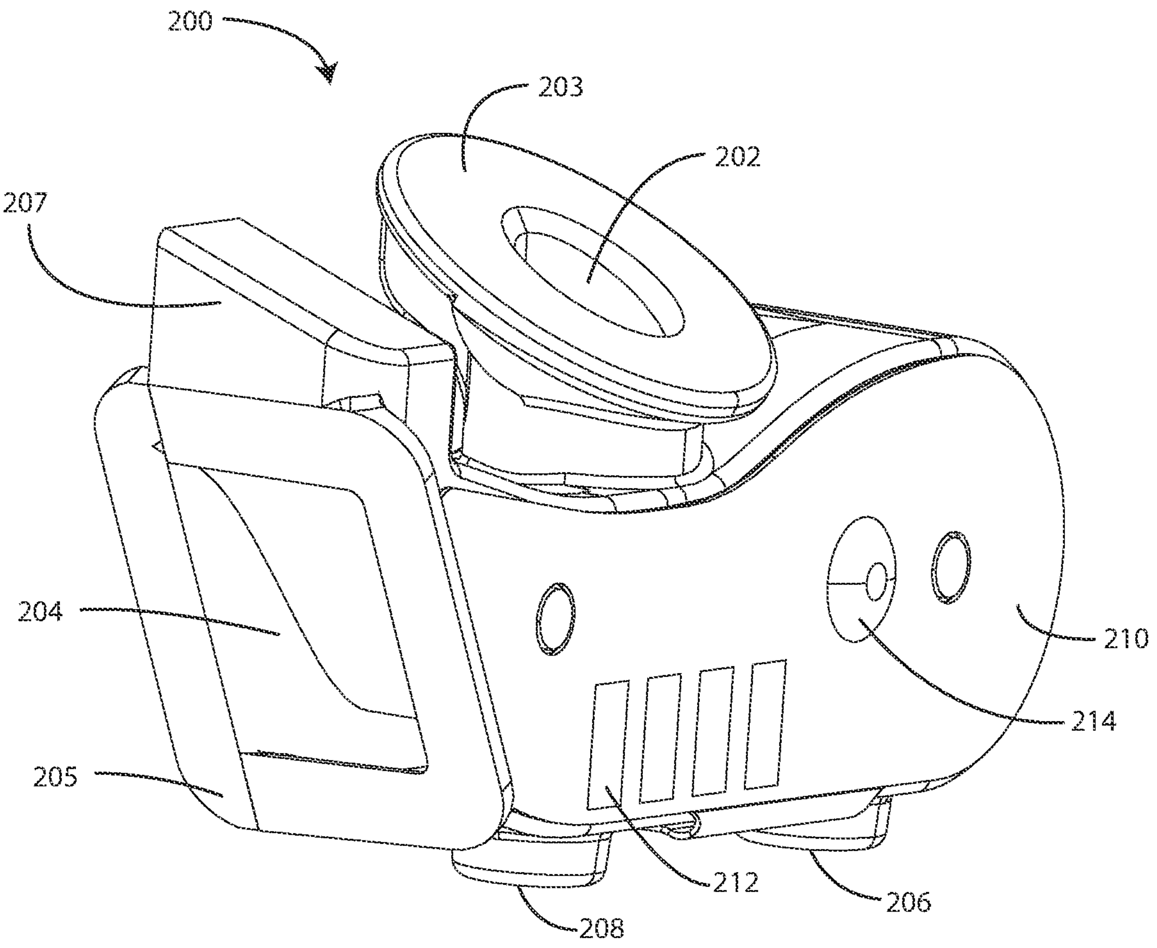
FIG. 2 is a perspective view of a breath path in accordance with various embodiments herein.
Figure 3:
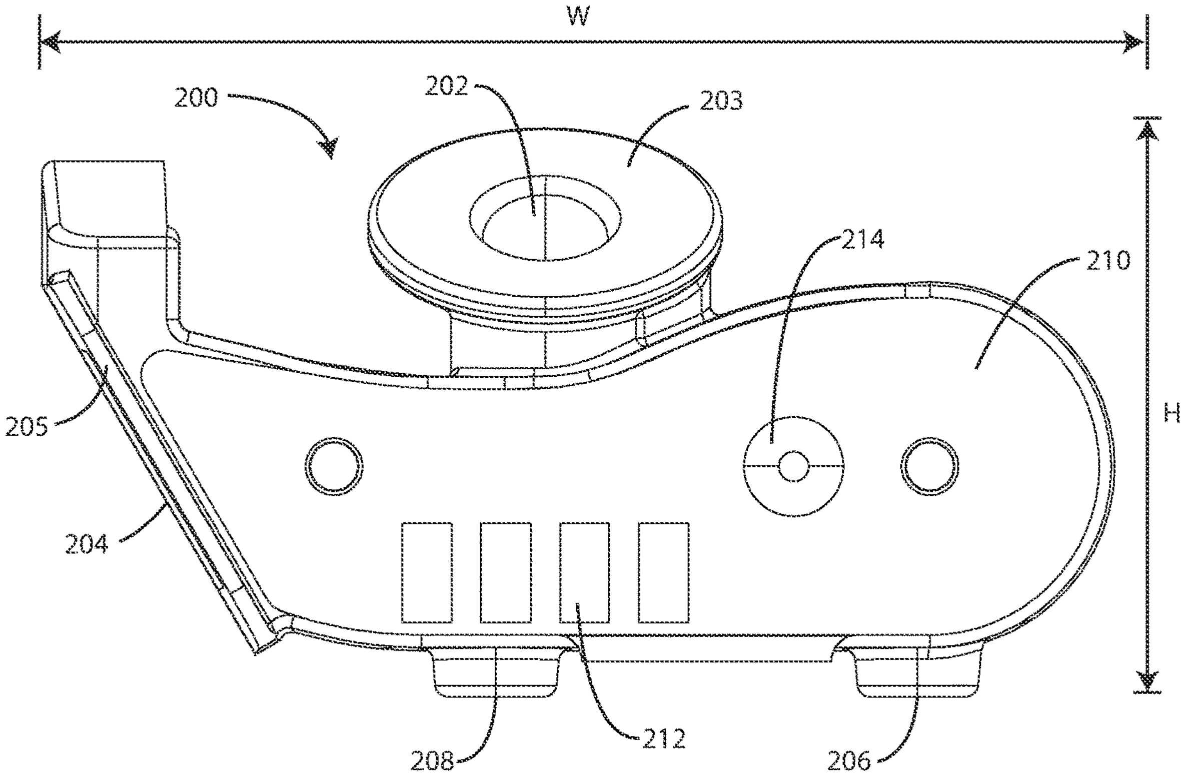
FIG. 3 is a front view of the breath path of FIG. 2 in accordance with various embodiments herein.
Figure 4:
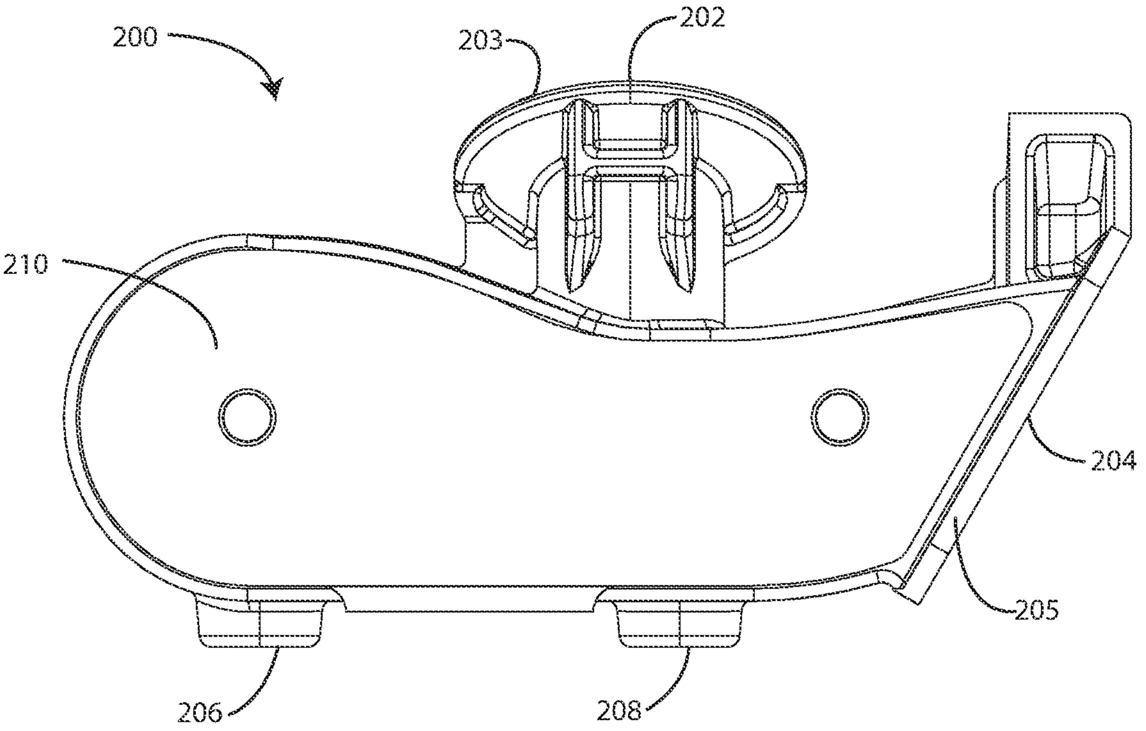
FIG. 4 is a rear view of the breath path of FIG. 2 in accordance with various embodiments herein.
Figure 5:
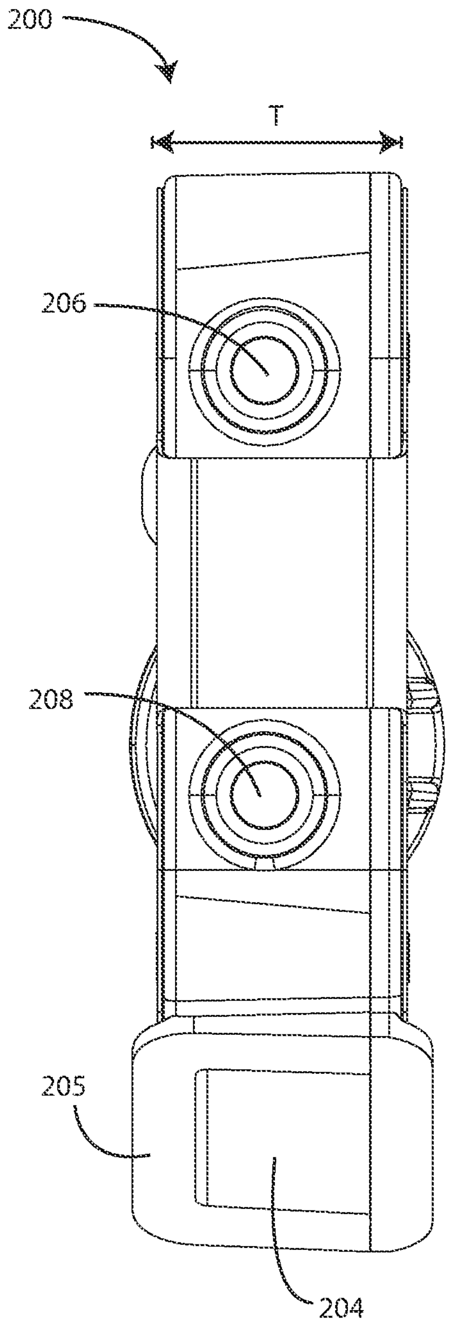
FIG. 5 is a bottom view of the breath path of FIG. 2 in accordance with various embodiments herein.

FIGS. 2-5 depict a breath path in accordance with various embodiments herein. FIG. 2, depicts a perspective view of a breath path, FIG. 3 depicts a front view of the breath path of FIG. 2, FIG. 4 depicts a rear view of the breath path of FIG. 2, and FIG. 5 depicts a bottom view of the breath path of FIG. 2 in accordance with various embodiments herein.

In various embodiments, the breath path 200 can be formed form any suitable material or materials including, but not limited to ductile plastics such as thermoplastics, blends of polyphenylene ether and polypropylene, or the like. In some embodiments the breath path 200 can be formed from thermally conductive materials such as thermally conductive plastics, or the like.

Referring now to FIG. 3, the breath path 200 can define a breath path width W and a breath path height H. In some embodiments, the breath path height H can be greater than or equal to 15, 17, 19, 21, or 23 mm. In some embodiments, the breath path height H can be less than or equal to 30, 28, 26, 25, or 23 mm. In some embodiments, the breath path height H can fall within a range of 15 to 30 mm, or 17 to 28 mm, or 19 to 26 mm, or 21 to 25 mm, or can be about 23 mm. In some embodiments, the breath path width W can be greater than or equal to 30, 33, 36, 40, or 43 mm. In some embodiments, the breath path width W can be less than or equal to 50, 48, 46, 45, or 43 mm. In some embodiments, the breath path width W can fall within a range of 30 to 50 mm, or 33 to 48 mm, or 36 to 46 mm, or 40 to 45 mm, or can be about 43 mm.

Referring now to FIG. 5, the breath path 200 can define a breath path thickness T. In some embodiments, the breath path thickness T can be greater than or equal to 10, 11, or 12 mm. In some embodiments, the breath path thickness T can be less than or equal to 15, 14, 13, or 12 mm. In some embodiments, the breath path thickness T can fall within a range of 10 to 15 mm, or 11 to 13 mm, or can be about 12 mm.

The breath path 200 can include a breath path inlet 202 (best seen in FIGS. 2-3). The breath path inlet 202 is configured to align with a housing inlet in the top hatch 110 of the alcohol detection device housing 102. In various embodiments, a center point of breath path inlet 202 is configured to align with a center point of the housing inlet. In various embodiments, the alignment between the center points of the breath path inlet 202 and housing inlet can have an offset up to a threshold. In some embodiments, the offset threshold can be less than or equal to 10, 8, 6, 4, 2, or 1% of the breath path height H or can be an amount falling within a range between any of the foregoing.

The breath path can include a breath path outlet 204. The breath path outlet 204 is configured to align with a housing outlet in one of a left-side housing wall portion or a right-side housing wall portion of the alcohol detection device housing 102. In various embodiments, a center point of breath path outlet 204 is configured to align with a center point of the housing outlet. In various embodiments, the alignment between the center points of the breath path outlet 204 and housing outlet can have an offset up to a threshold. In some embodiments, the offset threshold can be less than or equal to 10, 8, 6, 4, 2, or 1% of the breath path height H or can be an amount falling within a range between any of the foregoing.

In various embodiments, a breath sample provided by a user is received by the breath path 200 at the breath path inlet 202 and at least a portion of the breath sample exits the breath path through the breath path outlet 204.

In various embodiments, the breath path inlet 202 includes a breath path inlet gasket 203 surrounding at least a portion of the breath path inlet and the breath path outlet 204 includes a breath path outlet gasket 205 surrounding at least a portion of the breath path outlet. The path inlet gasket 203 and the path outlet gasket 205 are configured to form a seal with portions of the alcohol detection device housing 102 and can be made from any suitable material or materials, including, but not limited to rubbers, foams, or the like.

The breath path 200 can include a first breath path port 206 and a second breath path port 208 (best seen in FIG. 5). As will be described in greater detail herein, as the breath sample travels from the breath path inlet 202 to the breath path outlet 204, a first portion of the breath path will flow into the first breath path port 206. The first breath path port 206 is in fluid communication with a first pressure sensor, which can measure a first pressure value of the breath sample. A second portion of the breath sample will be pulled into the second breath path port 208, which is in fluid communication with a second pressure sensor, which can measure a second pressure value of the breath sample.

The breath path 200 can include a breath path heater 210 (best seen in FIGS. 2-3). In various embodiments, the breath path heater 210 is configured to surround at least a portion of the breath path 200. In various embodiments, the breath path heater 210 is removably connected to the breath path 200 such that the breath path heater can be removed from the breath path without damaging the breath path or the breath path heater. The breath path heater 210 may be attached to the breath path 200 using adhesive. The breath path heater can include one or more breath path heater contact pads 212. In various embodiments, the breath path heater contact pads 212 are electrical contacts and are configured to receive power from a first circuit board of the alcohol detection device 100. In various embodiments, the breath path heater 210 can include a temperature sensor 214 configured to measure a temperature of the breath path. The breath path heater is configured to heat the breath path as a function of the breath path temperature sensed by the temperature sensor 214.

The breath path also includes a protrusion 207 (FIG. 2) above the breath path outlet 204. The protrusion 207 is configured to contact a compressive material which in turn contacts the top hatch 110 (FIG. 1) so that the top hatch 110 applies pressure to the protrusion 207 through the compressible material, where the compressible material absorbs distance variation between the breath path and the top hatch to ensure the appropriate pressure is applied to the breath path despite any potential manufacturing variation. The pressure applied to the protrusion 207 by the top hatch 110 causes the structure of the breath path at the breath path outlet 204 to be pressed into a sealing engagement with the housing.

Figure 6:
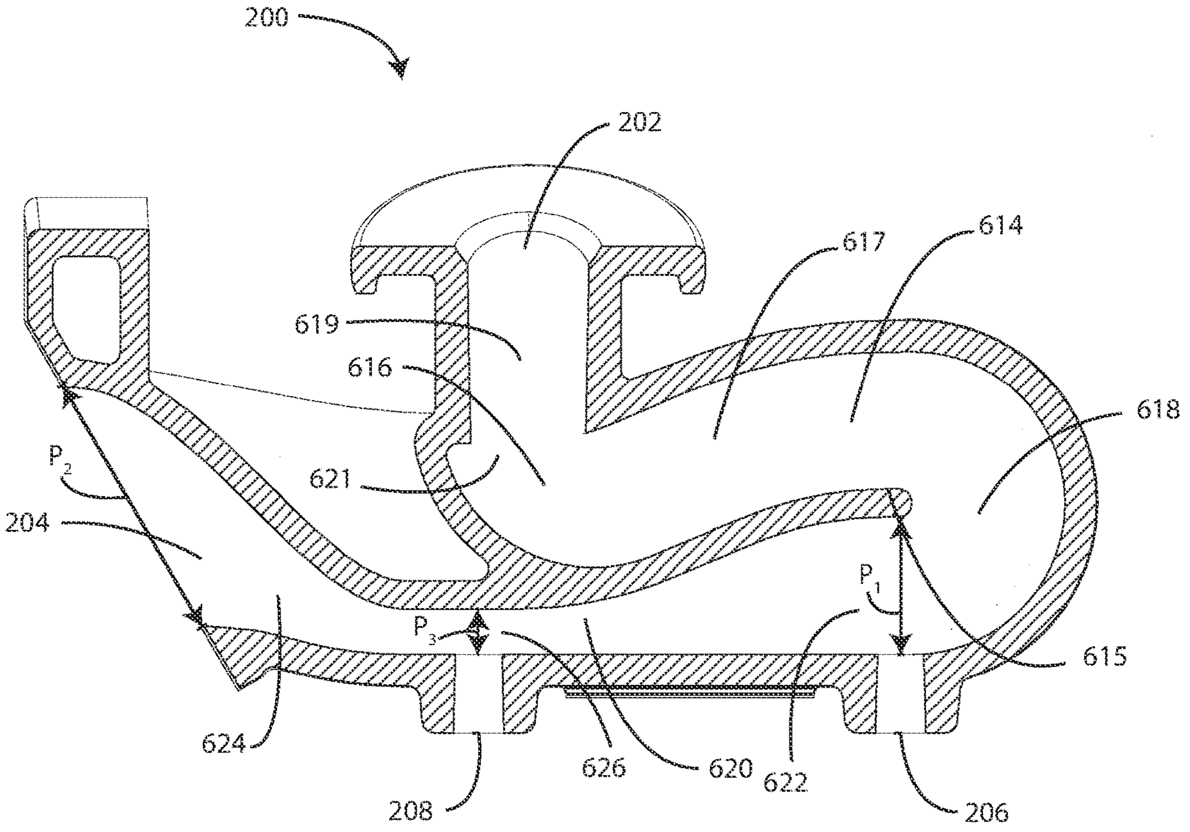
FIG. 6 is a cross-sectional view of the breath path of FIG. 2 in accordance with various embodiments herein.

Referring now to FIG. 6, a cross-sectional view of the breath path of FIG. 2 is shown in accordance with various embodiments herein. The breath path 200 can define a breath path space 614, which is the space enclosed by the breath path 200 through which the breath sample travels. In various embodiments, the breath path space 614 is defined by one or more breath path walls 615. The breath path walls 615 define a flow channel for the breath sample.

The breath path 200 can include a first bend 616 and a second bend 618. An inlet portion 619 can extend longitudinally from the breath path inlet 202 to an inlet portion end 621. The breath path can further include a first downstream portion 617 extending from the inlet portion end 621 toward a second bend 618. In various embodiments, the first bend 616 is disposed between the breath path inlet 202 and the breath path outlet 204. The first bend 616 can have a first bend angle measured between a longitudinal axis of the breath path inlet 202 and a longitudinal axis of a first downstream portion 617. In some embodiments, the angle of the first bend can be greater than or equal to 70, 80, or 90 degrees. In some embodiments, the angle of the first bend can be less than or equal to 110, 100, or 90 degrees. In some embodiments, the angle of the first bend can fall within a range of 70 to 110 degrees, or 80 to 100 degrees, or can be about 90 degrees. In other embodiments, the angle could be any single or compound angle necessary to direct the breath fluid flow to one side such that a subsequent bend could fold the flow back the other direction, forming a serpentine path which retains a desired over-all flow channel length, but in a more compact area.

The breath path 200 can include a second bend 618 disposed between the first bend 616 and the breath path outlet 204. The second bend 618 can have a second bend angle measured between an elongate portion 620 of the breath path 200 and the first downstream portion 617 of the breath path. In some embodiments, the angle of the second bend can be greater than or equal to 160, 170, or 180 degrees. In some embodiments, the angle of the second bend can be less than or equal to 200, 190, or 180 degrees. In some embodiments, the angle of the second bend can fall within a range of 160 to 200 degrees, or 170 to 190 degrees, or can be about 180 degrees.

The breath path 200 can include an elongate portion 620 disposed between the second bend 618 and the breath path outlet 204. In various embodiments, the elongate portion 620 runs about parallel to the top hatch 110 when the breath path 200 is inserted into the breath alcohol detection device 100. The elongate portion 620 can include a first portion 622 having a first cross-sectional area. The elongate portion can include second portion 624 disposed between the first portion 622 and the breath path outlet 204, where the second portion 624 has a second cross-sectional area. The elongate portion 620 can include a restriction portion 626 disposed between the first portion 622 and the second portion 624 having a third cross-sectional area. In various embodiments, the third cross-sectional area is smaller than the first cross-sectional area and the second cross-sectional area. In various embodiments, a first pressure sensor (not visible in this view) can be in fluid communication with the first portion 622 of the breath path 200 through a first breath path port 206 and a second pressure sensor (not visible in this view) can be in fluid communication with the restriction portion 626 of the breath path through a second breath path port 208. The first pressure sensor is configured to measure a first pressure value of the breath sample and the second pressure sensor is configured to measure a second pressure value of the breath sample.

In various embodiments, first portion 622 has a first exemplary cross-sectional area taken at plane $P_1$ parallel to the center of the first breath path port 206. In some embodiments, the first exemplary cross-sectional area can be greater than or equal to 30, 33, 35, or 38 $mm^2$. In some embodiments, the first exemplary cross-sectional area can be less than or equal to 50, 46, 42, or 38 $mm^2$. In some embodiments, the first exemplary cross-sectional area can fall within a range of 30 to 50 $mm^2$, or 33 to 46 mm, or 35 to 42 mm, or can be about 38 $mm^2$.

In various embodiments, the second portion 624 has a second exemplary cross-sectional area taken at plane $P_2$ parallel to the breath path outlet 204. In some embodiments, the second exemplary cross-sectional area can be greater than or equal to 70, 73, 75, or 78 mm. In some embodiments, the second exemplary cross-sectional area can be less than or equal to 90, 86, 82, or 78 $mm^2$. In some embodiments, the second exemplary cross-sectional area can fall within a range of 70 to 90 $mm^2$, or 73 to 86 $mm^2$, or 75 to 82 $mm^2$, or can be about 78 $mm^2$.

In various embodiments, restriction portion 626 has a third exemplary cross-sectional area taken at plane $P_3$ parallel to the center of the second breath path port 208. In some embodiments, the third exemplary cross-sectional area can be greater than or equal to 8, 9, 11, or 12 $mm^2$. In some embodiments, the third exemplary cross-sectional area can be less than or equal to 16, 15, 13, or 12 $mm^2$. In some embodiments, the third exemplary cross-sectional area can fall within a range of 8 to 16 $mm^2$, or 9 to 15 $mm^2$, or 11 to 13 $mm^2$, or can be about 12 $mm^2$.

In various embodiments, the ratio between the first exemplary cross-sectional area and the third exemplary cross-sectional area can be greater than or equal to 2, 2.5, or 3. In some embodiments, the ratio between the second exemplary cross-sectional area and the third exemplary cross-sectional area can be less than or equal to 5, 4, or 3. In some embodiments, the ratio between the second exemplary cross-sectional area and the third exemplary cross-sectional area can fall within a range of 2 to 3, or 2 to 4, or 3 to 4, or can be about 3.25.

In various embodiments, the ratio between the second exemplary cross-sectional area and the third exemplary cross-sectional area can be greater than or equal to 4, 5, 6, or 6.5. In some embodiments, the ratio between the second exemplary cross-sectional area and the third exemplary cross-sectional area can be less than or equal to 10, 8, 7, or 6.5. In some embodiments, the ratio between the second exemplary cross-sectional area and the third exemplary cross-sectional area can fall within a range of 4 to 10, or 5 to 8, or 6 to 7, or can be about 6.5.

Having multiple bends in the breath path 200 results in a winding flow channel turning approximately 90 degrees to the side at the first bend 616, then doubling back approximately 180 degrees at the second bend 618. Such a configuration gives the breath path 200 the same effective length as a straight breath of equivalent length while taking up less space in the alcohol detection device. In various embodiments, breath path 200 is configured to fit within the top fifth of the total length of the alcohol detection device housing 102. The alcohol detection device can have a total housing length $L_H$ defined from a bottom surface of the housing 102 to the top surface of the top hatch 110 (see FIG. 1) and a breath path length $L_B$ defined from a bottom surface of the breath path 200 to the top surface of the top hatch 110 (see FIG. 10). In some embodiments, the ratio of $L_B/L_H$ can be greater than or equal to 0.10, 0.15, 0.20, or 0.25. In some embodiments, the ratio of $L_B/L_H$ can be less than or equal to 0.50, 0.40, 0.25, or 0.20. In some embodiments, the ratio of $L_B/L_H$ can fall within a range of 0.10 to 0.50, or 0.15 to 0.40, or 0.20 to 0.30, or can be about 0.20.

Such a configuration leaves more flexibility for the placement of other electrical components within the alcohol detection device housing 102 such as a breath alcohol detection device, or the like. The winding shape of the breath path 200 also reduces the external surface area and overall mass of the breath path compared to a straight breath path of equivalent length. This improves thermal efficiency of the breath path 200 as less energy is required to heat the breath path to its desired temperature.

In various embodiments, the flow channel of the breath path 200 is substantially rectangular in cross section. While not intending to be bound by theory and not describing all situations, it is believed, that a rectangular flow channel allows more efficient geometric packing of the breath path than a circular cross-section. However, the flow channel of the breath path can be any other suitable cross-sectional shape such as circular, or the like.

Breath Path Heater

Figure 7:
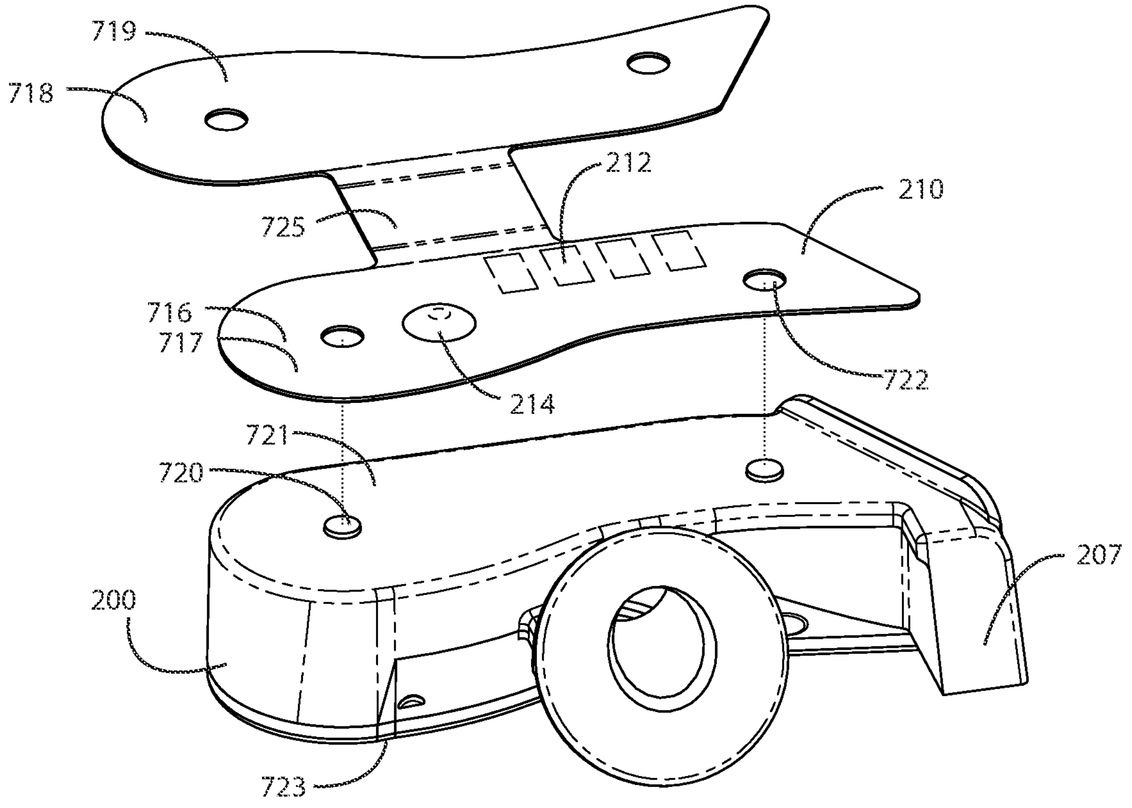
FIG. 7 is a perspective view of the breath path with the heater removed in accordance with various embodiments herein.

Referring now to FIG. 7, a perspective view of the breath path with the heater removed is shown in accordance with various embodiments herein. In various embodiments the breath path can have a breath path heater 210 configured to wrap around an outside portion of the breath path 200. In various embodiments the breath path heater 210 can include a first heater portion 716 having a first resistive heating element 717, a second heater portion 718 having a second resistive heating element 719, and a connecting portion 725 joining the first heater portion and second heater portion. A resistive heating element as defined herein is any device that converts electrical energy into heat by passing an electric current through a conductor.

In various embodiments, the first heater portion 716 is shaped to have approximately the same perimeter as a first surface 721 of the breath path 200 and is configured to cover first surface 721 when attached to the breath path. In some embodiments, the first heater portion 716 can cover at least 75, 80, 85, 90, 95, or 100% of the first surface 721 of the breath path 200. In various embodiments, the second heater portion 718 is shaped to have approximately the same perimeter as a second surface 723 of the breath path 200 and is configured to cover the second surface 723 when attached to the breath path. In some embodiments, the second heater portion 718 can cover at least 75, 80, 85, 90, 95, or 100% of the second surface 723 of the breath path 200. In various embodiments, the first surface 721 is on an opposite side of the breath path 200 from the second surface 723.

In various embodiments, the connecting portion 725 is configured to join the first heater portion 716 and second heater portion 718 of the breath path heater 210. The connecting portion 725 is shaped and sized so as not to obstruct the first breath path port 206 or the second breath path port 208. In various embodiments, the connecting portion 725 does not contain a resistive heating element specifically meant to heat the connecting surface. In various embodiments, the connecting portion 725 has electrical traces, which may give off heat, to allow electric current to flow from one side to the other. Alternatively, in some embodiments, the connecting portion 725 may contain a third resistive heating element, with the purpose of heating the surface covered by the connecting portion.

The breath path heater 210 can include the one or more breath path heater contact pads 212. In various embodiments, the breath path heater contact pads 212 are configured to receive power from a first circuit board of the alcohol detection device 100. In various embodiments, the breath path heater 210 can include a temperature sensor 214 configured to measure a temperature of the breath path. The breath path heater 210 is configured to provide heat to the breath path 200 as a function of the breath path temperature sensed by the temperature sensor 214.

In various embodiments, the breath path heater comprises a flexible circuit board. The flexible circuit board houses the first resistive heating element 717 and the second resistive heating element 719 and is electrically connected to the first circuit board of the alcohol detection device 100 via the one or more breath path heater contact pads 212 disposed on breath path heater 210. In various embodiments, a controller electrically connected to the first circuit board is configured to control the first resistive heating element 717 and the second resistive heating element 719. The controller is configured receive a temperature value from the temperature sensor 214 as an input and to adjust the level of heat delivered by the first resistive heating element 717 and the second resistive heating element 719 to the breath path 200 accordingly. While not intending to be bound by theory and not describing all situations, it is believed that heating and maintaining the breath sample to a temperature between 35° C. and 40° C. prevents the breath sample from condensing on the walls of the breath path, resulting in more accurate alcohol detection results.

In various embodiments, the first resistive heating element 717 and the second resistive heating element 719 are in series with one and other on the flexible circuit board and are controlled together, such that the first resistive heating element 717 and the second resistive heating element 719 are configured to heat to the same temperature on their respective sides of the breath path 200 at any given time. The two heaters in series can also be configured to product different amounts of heat to each side depending on the relative amount of heating element on each side, and has the characteristic that heat could be adjusted to both heating elements only in proportion to each other. Alternatively, the first resistive heating element 717 and the second resistive heating element 719 are controlled independently such that the first heater resistive heating element and the second heater resistive heating element can provide varying levels of heat to their respective sides of the breath path 200 at any given time. In this embodiment, the first resistive heating element 717 and the second resistive heating element 719 can be heated to different temperatures and for different lengths of time if desired.

Figure 8:
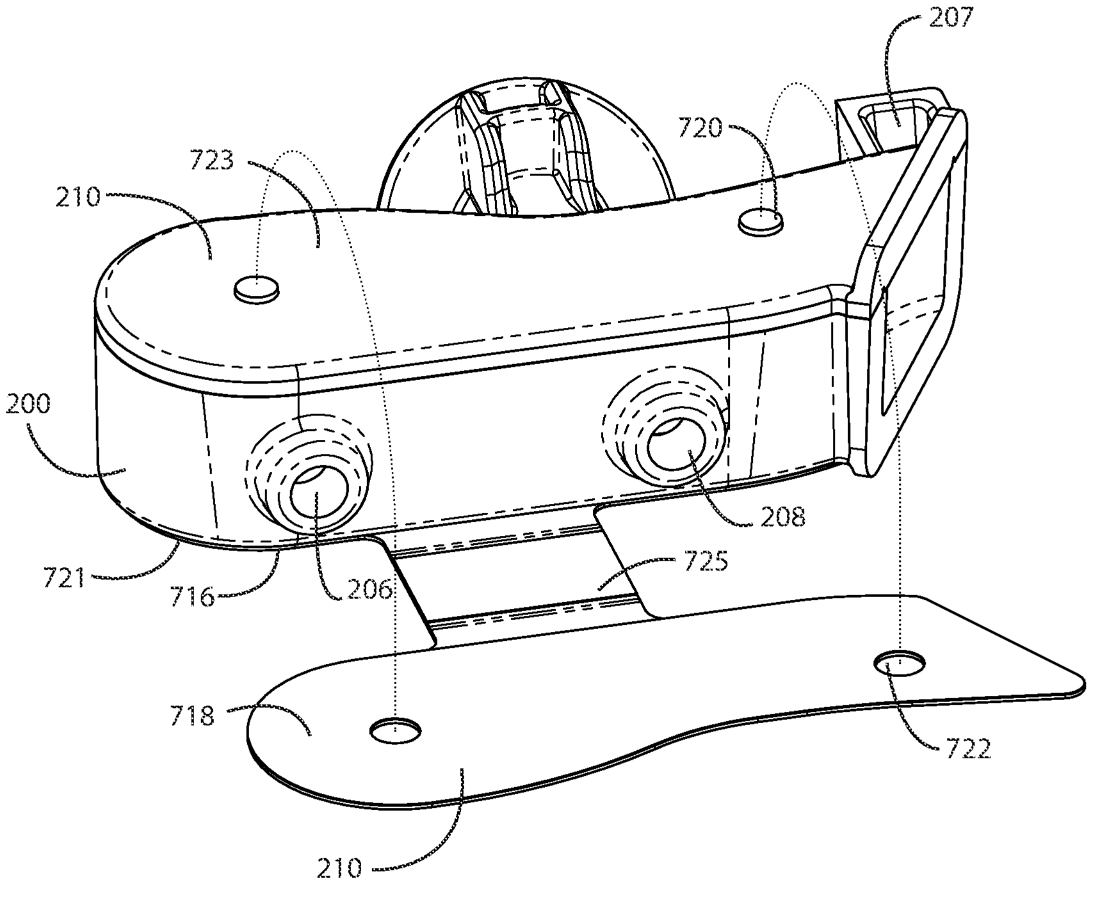
FIG. 8 is a perspective view of the breath path with the heater partially assembled in accordance with various embodiments herein.

Referring now to FIG. 8, a perspective view of the breath path with the heater partially assembled is shown in accordance with various embodiments herein. In various embodiments, the first heater portion 716 is configured to removably attach to the first surface 721 of the breath path 200 and the second heater portion 718 is configured to removably attach to the second surface 723 of the breath path 200. In various embodiments, the breath path 200 can have one or more breath path attachment structures 720 and the breath path heater 210 can have one or more heater attachment structures 722. The breath path attachment structures 720 are configured to removably attach to the one or more heater attachment structures 722. The breath path attachment structures 720 and heater attachment structures 722 can be suitable structure or structures including, but not limited to one or more pairs of mating openings and raised structures, snaps, magnets, pins, and holes, or the like.

Handheld Breath Alcohol Detection Device

Figure 9:
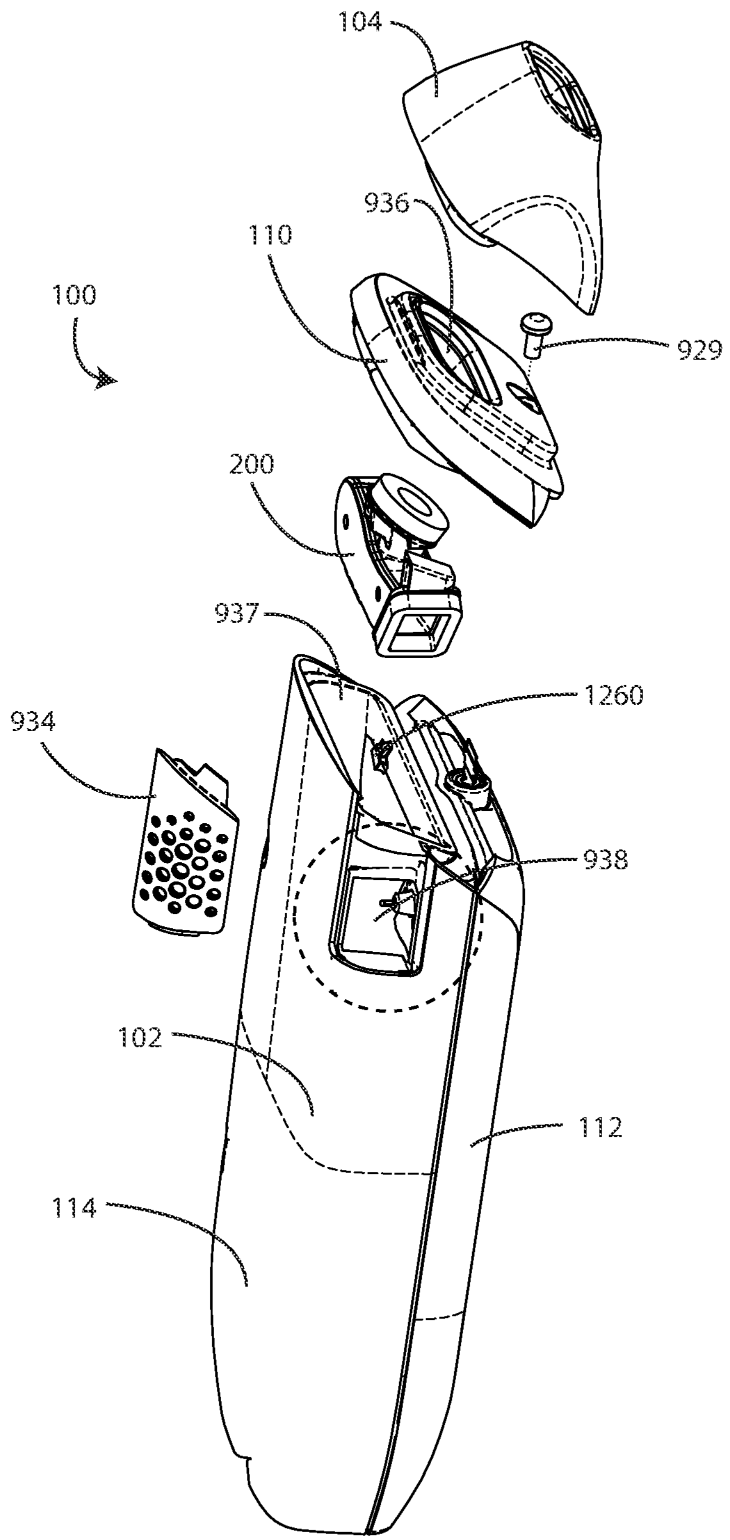
FIG. 9 is an exploded view of the breath alcohol detection device of FIG. 1 in accordance with various embodiments herein.

Referring now to FIG. 9, an exploded view of the breath alcohol detection device of FIG. 1 is shown in accordance with various embodiments herein. In various embodiments, the breath alcohol detection device 100 is sized to fit comfortably in a human hand. In various embodiments, the breath alcohol detection device 100 can include a housing 102 formed from a top hatch 110, a front housing 112, and a rear housing 114. The housing 102 can have a housing inlet 936 within the top hatch 110 of the housing. The housing 102 can have a housing outlet 938 defined in one of the left or right sides of the housing. The housing outlet can be covered by a housing outlet cover 934 removably attached to the housing 102, but means of a friction fit, or the like. In another embodiment, the housing outlet cover may be integrated into the housing side and the housing outlet be a separate piece that is retained by a friction fit or the like to the inside of the housing. The breath alcohol detection device 100 can further include a mouthpiece 104. Mouthpiece 104 can have mouthpiece inlet 105 configured to align with the housing inlet 936, such that a breath sample can be provided at the mouthpiece and enter the alcohol detection device 100 via that mouthpiece inlet 105 and the housing inlet 936.

In various embodiments, the top hatch 110 can be removably attached to the housing 102 with a threaded fastener 929 or by other means such as a friction fit. In various embodiments, the top hatch 110 is removable from the housing 102 by removing threaded fastener 929 from a first side of the top hatch and pivoting the top hatch about the first side. In various embodiments, after removing the top hatch 110, the breath path 200 can be pulled out from a top hatch opening 937 of the breath alcohol detection device 100. In some examples, the breath path 200 can be removed from the breath alcohol detection device 100 without the use of tools, other than any tools used to remove the top hatch. Alternatively, removing the breath path 200 from the breath alcohol detection device 100 may require the use of one or more tools available at a service or repair center. In some embodiments, upon removing the top hatch, the breath path 200 can be removed without causing damage to the breath path 200 or the breath alcohol detection device 100. In some embodiments, the breath path 200 can be removed without disconnecting the front housing 112 from the rear housing 114. In some embodiments, a new breath path 200 can be installed in the breath alcohol detection device without disconnecting the front housing 112 from the rear housing 114.

Figure 10:
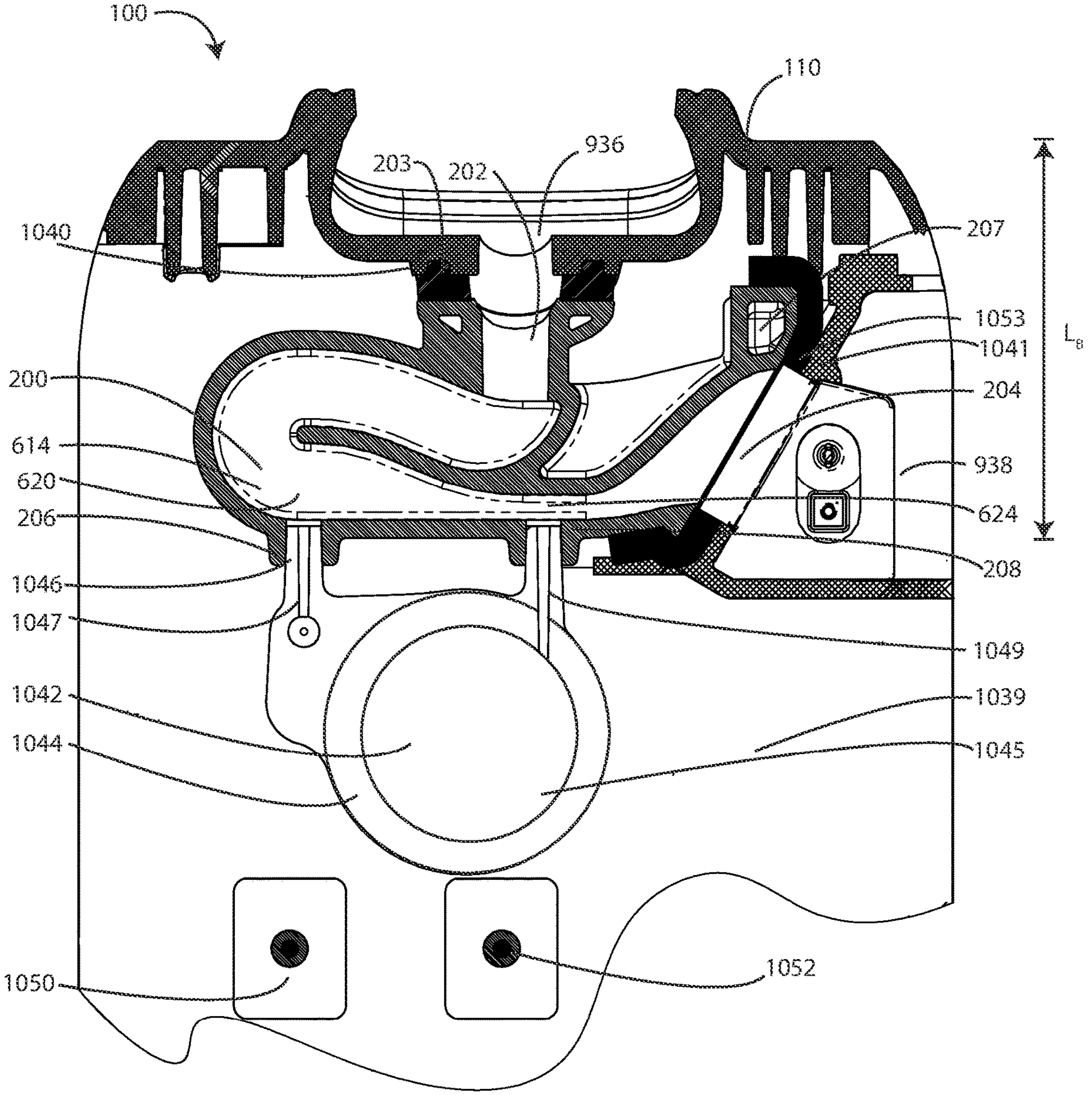
FIG. 10 is a cross-sectional view of the breath alcohol detection device of FIG. 1 in accordance with various embodiments herein.

Referring now to FIG. 10, a cross-sectional view of the breath alcohol detection device of FIG. 1 is shown in accordance with various embodiments herein. In various embodiments, the breath path inlet 202 includes a breath path inlet gasket 203 surrounding at least a portion of the breath path inlet. In various embodiments, the top hatch 110 includes a top hatch gasket sealing surface 1040 surrounding at least a portion of the housing inlet 936. The breath path inlet gasket 203 is configured to form a seal with the top hatch gasket sealing surface 1040 when the top hatch 110 is secured to the breath alcohol detection device housing 102. When the top hatch is closed, the top hatch gasket sealing surface 1040 compresses the breath path inlet gasket 203. In various embodiments, the top hatch gasket sealing surface 1040 defines a channel that traps a portion of the breath path inlet gasket 203.

In various embodiments breath path outlet 204 includes a breath path outlet gasket 205 surrounding at least a portion of the breath path outlet. In various embodiments, the housing outlet 938 includes a housing outlet gasket sealing surface 1041 surrounding at least a portion of the housing outlet. The breath path outlet gasket 205 is configured to form a seal with the housing outlet gasket sealing surface 1041 when the top hatch 110 is secured to the breath alcohol detection device housing 102. In various embodiments, securing the top hatch 110 to the breath alcohol detection device 100 (by means of the threaded fastener 929 or the like) compresses the breath path inlet gasket 203 to the top hatch gasket sealing surface 1040 and compresses the breath path outlet gasket 205 to the housing outlet gasket sealing surface 1041, thus forming an air-tight seal between the breath path 200 and the alcohol detection device housing 102.

In various embodiments, the breath path 200 can include a protrusion 207 disposed above the breath path outlet 204 and breath path outlet gasket 1053. The embodiment of FIG. 10 shows an alternative embodiment of the breath path outlet gasket 1053 in which the breath path outlet gasket 1053 wraps around the protrusion 207 and the breath path 200. In one embodiment, the device 100 is configured so that the top hatch 110 applies pressure to the protrusion 207 upon being attached to the remainder of the housing 102. In the embodiment of FIG. 10, the top hatch 110 squeezes the outlet gasket 1053 against the protrusion 207 and the breath path 200. In addition, or alternatively, the top hatch 110 can contact the protrusion 207 directly. The pressure applied to the protrusion 207 by the top hatch 110 causes breath path outlet gasket 1053 to be pressed into a sealing engagement with the breath path outlet gasket sealing surface 1041.

The breath path outlet 204 and the breath path outlet gasket 1053 are angled with respect to the sidewalls of the housing of the alcohol detection device. The angle of breath path outlet 204 and the breath path outlet gasket 205 is best illustrated in FIGS. 3-4. Referring again to FIG. 10, the housing outlet gasket sealing surface 1041 is angled to complement the angle of the breath path outlet 204 and breath path outlet gasket 1053. This arrangement allows for the breath path 200 to be lifted out of engagement with the housing outlet gasket sealing surface 1041 without shearing forces being applied to the breath path outlet gasket 1053, as might be the case if the breath path outlet gasket 1053 sealed directly against an inner wall of the housing and were not angled.

In various embodiments, the breath alcohol detection device 100 can include a breath alcohol sensor 1042 in fluid communication with the breath path space 614. The breath alcohol sensor 1042 can further include a breath alcohol sensor housing 1044 having a first breath alcohol sensor port 1046 and a second breath alcohol sensor port 1048. In various embodiments, the first breath alcohol sensor port 1046 and the second breath alcohol sensor port 1048 are in fluid communication with the breath path space 614. In one example, the first breath path port 206 is configured to interface with the first breath alcohol sensor port 1046 and the second breath path port 208 is configured to interface with the second breath alcohol sensor port 1046, such that the first and second breath alcohol sensor ports are sized to fit within and form a seal with the first and second breath path ports. In an embodiment the first and second breath alcohol sensor ports have a substantially conical exterior profile and the first and second breath path ports have a substantially conical interior profile such that the first and second breath alcohol sensor ports are sized to engage in a friction fit with the first and second breath path ports. In various embodiments, the first and second breath alcohol sensor ports and the first and second breath path ports are formed from one or more ductile materials and the first and second breath alcohol sensor ports and the first and second breath path ports are configured to conform to one and other and form a seal. The first and second breath alcohol sensor ports and the first and second breath path ports can be formed form any suitable material or materials including, but not limited to ductile plastics such as thermoplastics, blends of polyphenylene ether and polypropylene, or the like.

In various embodiments, securing the top hatch 110 to the breath alcohol detection device 100 (by means of the threaded fastener 929 or the like) compresses the first breath path port 206 onto the first breath alcohol sensor port 1046 and compresses the second breath path port 208 onto the second breath alcohol sensor port 1048. This forms an airtight seal between the breath path space 614 and the breath alcohol sensor 1042. In some embodiments, the top hatch gasket sealing surface 1040 is configured to compress the breath path inlet gasket 203. The compressed breath path inlet gasket 203 can provide an additional spring force to push the first and second breath alcohol sensor ports into the first and second breath path ports.

In various embodiments, first breath path port is 1046 in fluid communication with a first pressure sensor 1050 through the first breath alcohol sensor port 1046 and a bypass path 1047 in the breath alcohol sensor housing 1044. The bypass path 1047 is configured to bypass the breath alcohol sensor 1042 and route a first portion of the breath sample from the first portion 622 of the breath path 200 to the first pressure sensor 1050. The first pressure sensor 1050 is configured to measure a first pressure value of the breath sample from the first portion 622 of the breath path 200. In various embodiments, the second breath path port 208 is in fluid communication with the second pressure sensor 1052 through the second breath alcohol sensor port 1048 and the breath alcohol sensor 1042. The second pressure sensor 1052 is configured to measure a second pressure value of the breath sample from the restriction portion 626 of the breath path 200.

Taking a first pressure value with the first pressure sensor 1050 from a first portion 622 of the breath path 200 and a second pressure value with the second pressure sensor 1052 from a restriction portion 626 of the breath path (with the restriction portion having a smaller cross-sectional area than the first portion) allows for the flow rate of the breath sample to be measured using Bernoulli's equation. The first pressure sensor 1050 and the second pressure sensor 1052 form a differential pressure flow meter that generates a flow measurement by measuring the pressure difference at two different locations in the elongate portion 620 of breath path 200. This pressure difference is created by constricting of the elongate portion 620 of the breath path 200 at the restriction portion 626, which causes an increase in flow velocity and a corresponding pressure drop. It is through these changes in the fluid flow that the volumetric flow rate can be deduced.

In various embodiments, the breath alcohol detection device 100 includes a one or more circuit boards, such as first circuit board 1039, and the breath alcohol sensor 1042 is electrically connected to the first circuit board 1039. The breath alcohol sensor 1042 contains components needed to detect alcohol content in a breath sample.

In various embodiments, the breath alcohol sensor 1042 is a fuel cell-type detector element and converts alcohol content within the breath sample to a measurable electrical signal. The breath alcohol sensor 1042 can include a sampling port 1049 configured to withdraw a portion of the breath sample from the breath path 200 to be tested for alcohol content. The sampling port 1049 provides a passage into a fuel cell 1045 of the breath alcohol sensor 1042. The fuel cell 1045 is configured to catalytically combine any alcohol in a sample introduced into the fuel cell through sampling port 1049 with oxygen to create an electrical signal that is amplified and measured to determine an alcohol concentration in the breath sample in a known fashion.

Although the fluid path between the first breath alcohol sensor port 1046 and the first pressure sensor 1050 passes through the breath alcohol sensor housing 1044, that fluid path does not connect to the fuel cell 1045. Instead, that fluid path to the first pressure sensor 1050 bypasses the fuel cell using the bypass path 1047.

Figure 11:
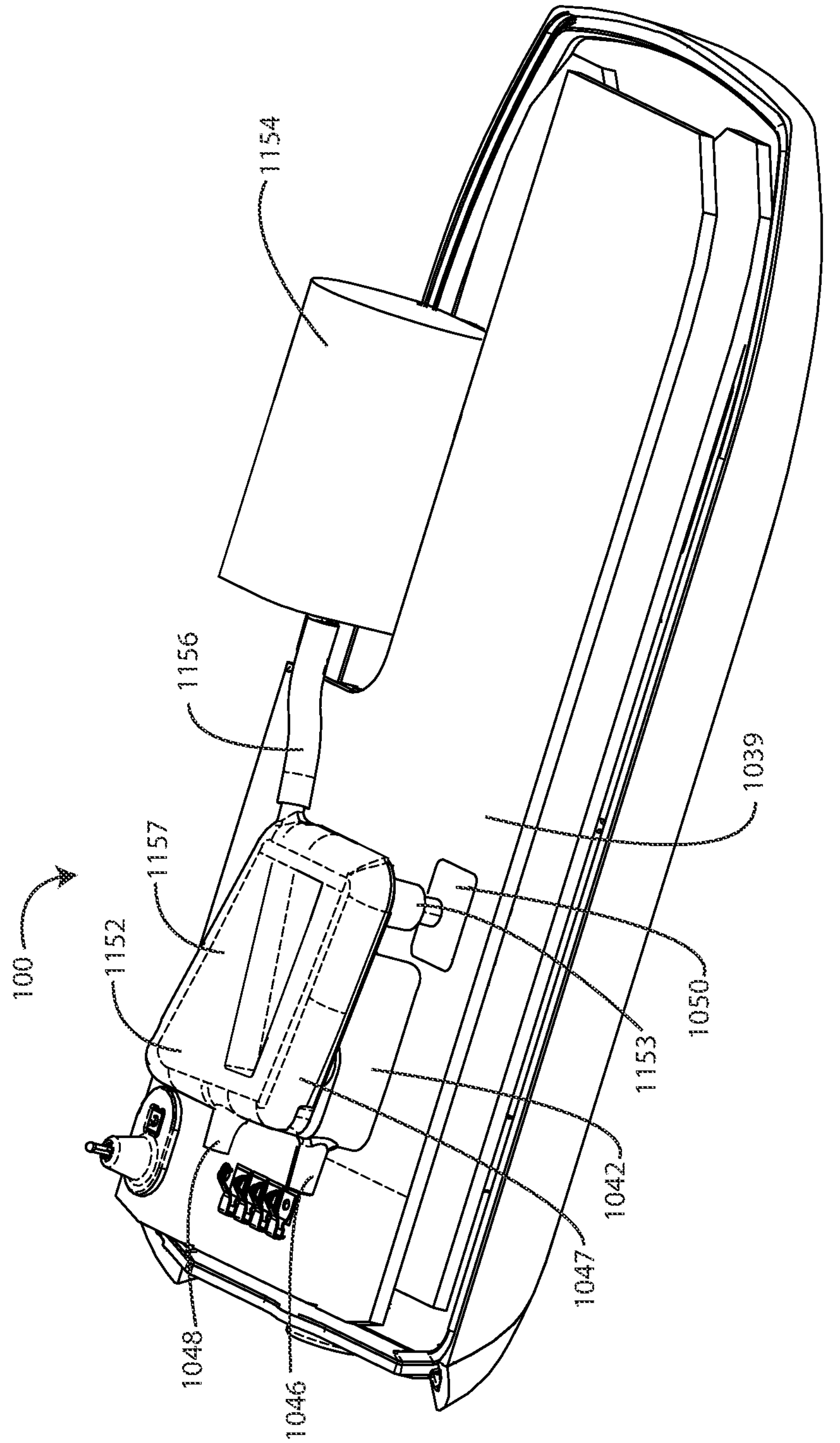
FIG. 11 is a perspective view of a subassembly of the breath alcohol detection device of FIG. 1 in accordance with various embodiments herein.

Referring now to FIG. 11, a perspective view of a subassembly of the breath alcohol detection device of FIG. 1 is shown in accordance with various embodiments herein. The subassembly does not include the rear housing, top hatch, or breath path, so that connections to the breath path and other components can be better illustrated. In various embodiments, the breath alcohol sensor 1042 can be fluidically connected to a manifold 1152. The bypass path 1047 can be housed within and defined by the manifold 1152 and is in fluid communication with the breath alcohol sensor housing 1044. In such embodiments, the first breath path port 206 (not shown in this view) is in fluid communication with a first pressure sensor 1050 through the first breath alcohol sensor port 1046 and the bypass path 1047, which routes the breath sample over the breath alcohol sensor 1042 and through the manifold 1152. The breath sample is then routed out through the first manifold outlet 1153 to the first pressure sensor 1050 to obtain a first pressure value of the breath sample.

In some embodiments, after a portion of the breath sample is pulled through sampling port 1049 and fuel cell 1045, the breath sample exits the fuel cell through a fuel cell outlet (not shown in this view) and enters a second manifold passage 1157, which is in fluid communication with the fuel cell outlet. The breath sample is then routed out through second manifold passage 1157 to the second pressure sensor 1052 to obtain a second pressure value of the breath sample. The breath sample is then routed to the pump 1154 through the alcohol sensor outlet 1156.

While the example of FIG. 11 depicts a manifold, it is possible to fluidically connect the first breath path port 206 to the first pressure sensor 1050 and the second breath path port 208 to the second pressure sensor 1052 though any suitable configuration of rigid tubing, flexible tubing, or a combination of rigid and flexible tubing.

In various embodiments, a pump 1154 is connected in fluid communication to the breath alcohol sensor 1042 by breath alcohol sensor outlet 1156. The breath alcohol sensor outlet 1156 can be housed in the manifold 1152 and fluidically connected to the breath alcohol sensor housing 1044. The pump 1154 is configured to supply a vacuum to the breath alcohol sensor 1042 at the opposite end of the sampling port 1049. The pump 1154 is configured to extract the desired sample volume of the breath sample from the breath path 200 and pull it through the breath alcohol sensor 1042.

The pump 1154 can be any suitable type of pump such as a bellows-type pump, or the like. The pump 1154 is used to selectively withdraw a test sample through the breath alcohol sensor 1042. The pump 1154 is preferably able to selectively provide either a vacuum or a positive pressure through the breath alcohol sensor outlet 1156. To withdraw a test sample through the breath alcohol sensor 1042 as described above, a vacuum is applied through the breath alcohol sensor outlet 1156. In order to assure no migration of the initial portion of a blow into the breath alcohol sensor 1042, it is preferred to provide a slight positive pressure through the breath alcohol sensor outlet 1156 prior pulling a breath sample into the breath alcohol sensor 1042.

Breath alcohol sensor 1042 may further include a heater (not pictured) configured to heat the breath alcohol sensor 1042 to a proper operating temperature. The heater may also include a temperature sensing mechanism. Preferably the temperature of the breath alcohol sensor 1042 is maintained at 34° C. to keep it above the sample temperature and to prevent condensation of water or vapors. The accuracy of the conversion process is also aided by maintaining a known temperature because the fuel cell catalytic process is temperature dependent.

Figure 12:
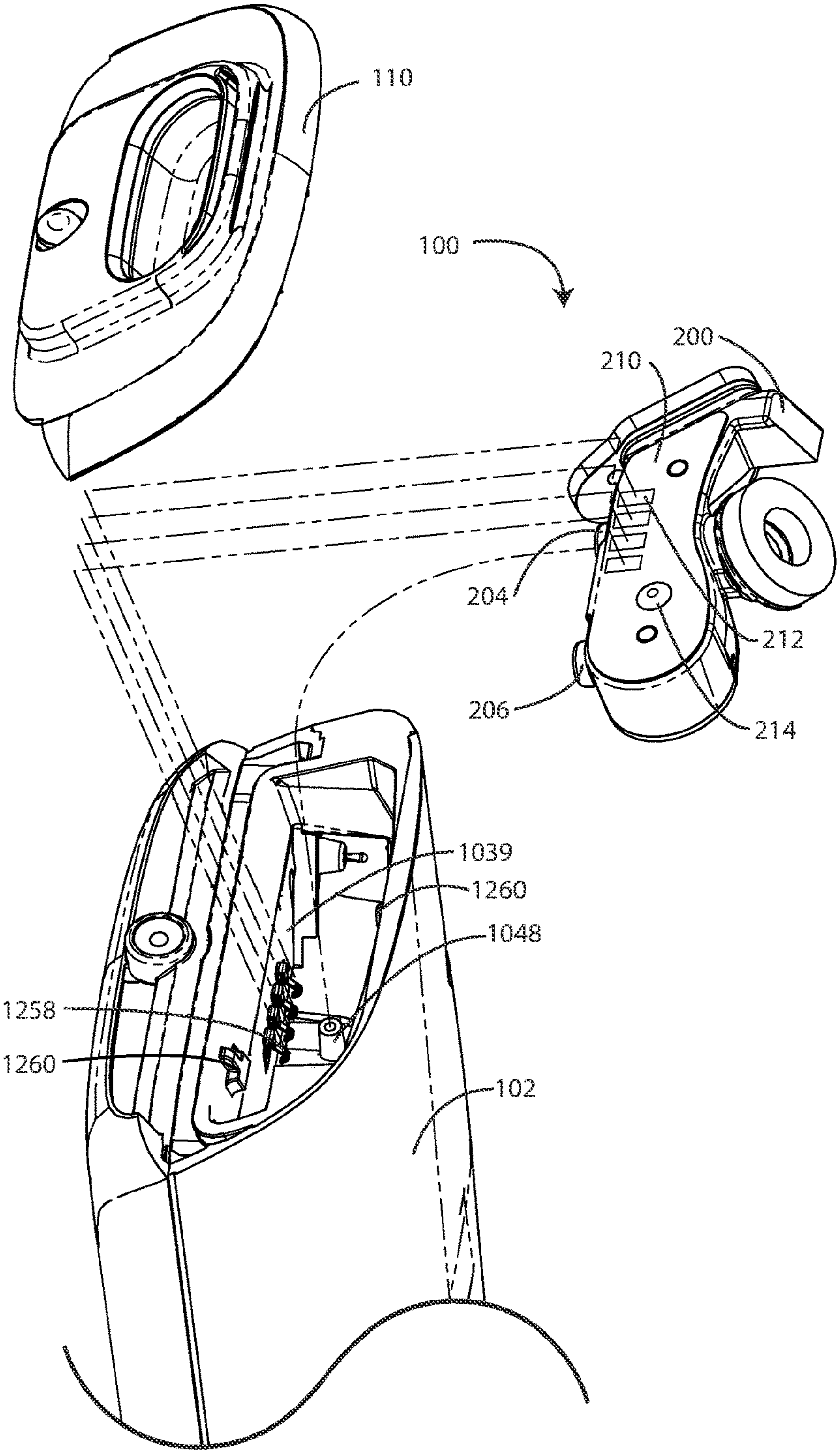
FIG. 12 is an exploded view of the breath alcohol detection device of FIG. 1 in accordance with various embodiments herein.

Referring now to FIG. 12, an exploded view of the breath alcohol detection device of FIG. 1 is shown in accordance with various embodiments herein. In various embodiments, the breath alcohol detection device housing 102 can include a plurality of ribs 1260 configured to align the breath path 200 to the housing 102 as the breath path is inserted into the housing. In some embodiments, the breath alcohol detection device housing 102 can include a plurality of ribs 1260 on opposed sides of the housing 102 such that the breath path 200 is supported by the ribs on both its front and rear sides. In one example, the plurality of ribs 1260 are configured to aid in aligning the breath path to the breath alcohol detection device such that first breath path port 206 aligns with the first breath alcohol sensor port 1046 and the second breath path port 208 aligns with the second breath alcohol sensor port 1048 as the breath path 200 is inserted into the housing 102.

In various embodiments, breath alcohol detection device 100 can contain a first circuit board 1039 disposed within the housing 102. The first circuit board 1039 can include one or more spring contacts 1258 electrically connected to the first circuit board. In various embodiments, a plurality of breath path heater contact pads 212 electrically connected to breath path heater 210 are configured to receive power from the plurality of spring contacts 1258 disposed on the first circuit board 1039. In various embodiments, the insertion of the breath path 200 causes the breath path heater contact pads 212 to compress the plurality of spring contacts 1258, forming an electrical connection between the breath path heater 210 and first circuit board 1039.

Figure 13:
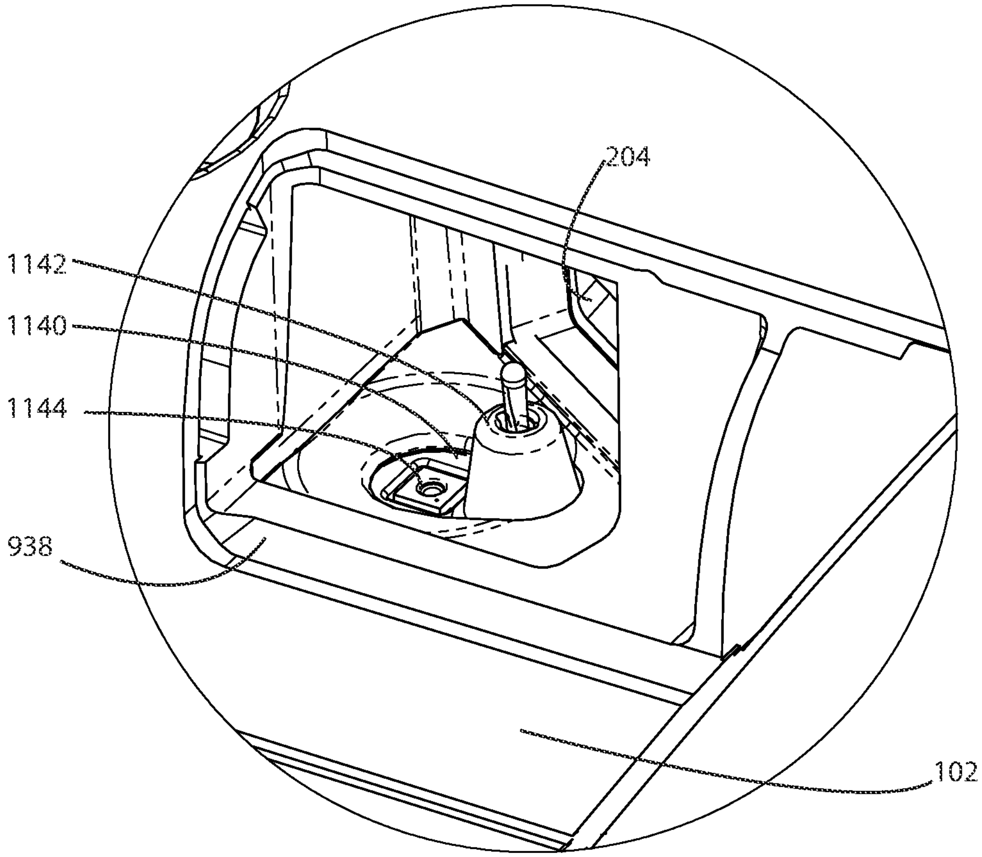
FIG. 13 is a perspective view of the housing outlet is shown in accordance with various embodiments herein in accordance with various embodiments herein.

Referring now to FIG. 13, a perspective view of the housing outlet is shown in accordance with various embodiments herein. In various embodiments, the alcohol detection device 100 can have a housing outlet 938 defined in one of the left or right sides of the housing 102. The breath path outlet 204 is configured to align with the housing outlet 938 such that a breath sample is configured to exit the breath alcohol detection device 100 through the breath path outlet 204 and the housing outlet 938.

In various embodiments, an anti-circumvention sensor assembly 1140 is disposed between the breath path outlet 204 and the housing outlet 938 such that the breath sample exits the breath path via the breath path outlet 204 and flows over the anti-circumvention sensor assembly before exiting the breath alcohol detection device 100 via the housing outlet 938. Although the example of FIG. 13 depicts the anti-circumvention sensor assembly 1140 located outside of the breath path 200, it is also possible for the anti-circumvention sensor assembly to be located within the breath path.

The anti-circumvention sensor assembly 1140 can include at least one of a temperature sensor 1142, a humidity sensor 1144, and a pressure sensor. In the example of FIG. 13, the anti-circumvention sensor assembly 1140 includes both a temperature sensor 1142 and a humidity sensor 1144. The anti-circumvention sensor assembly is configured to measure a temperature of the breath sample, a humidity of the breath sample, or both a temperature and a humidity of the breath sample.

The temperature sensor 1142 and humidity sensor 1144 can be used in a plurality of ways to analyze the breath sample characteristics and compare them to know characteristics. If the sensed characteristics vary too greatly from known characteristics, the sample is considered invalid and identified as a potential circumvention attempt.

In various embodiments, the temperature sensed by the temperature sensor 1142 is compared to the known temperature of human breath. If the sensed temperature varies too greatly from the known value, a circumvention attempt is detected. Similarly, in addition or alternatively, in various embodiments, the humidity sensed by the humidity sensor 1144 is compared to the known humidity of human breath. If the sensed humidity varies too greatly from the known value, a circumvention attempt is detected. In addition, or alternatively, in various embodiment, the system can used time-based analyses to identify circumventions, such as analysis of how quickly the temperature climbs or drops. These features can be used to detect if users employ a source of forced air instead of providing a breath sample into the breath alcohol detection device 100.

Methods

Many different methods are contemplated herein, including, but not limited to, methods of making, methods of using, and the like. Aspects of system/device operation described elsewhere herein can be performed as operations of one or more methods in accordance with various embodiments herein.

In various embodiments, operations described herein, and method steps can be performed as part of a computer-implemented method executed by one or more processors of one or more computing devices. In various embodiments, operations described herein, and method steps can be implemented instructions stored on a non-transitory, computer-readable medium that, when executed by one or more processors, cause a system to execute the operations and/or steps.

Figure 14:
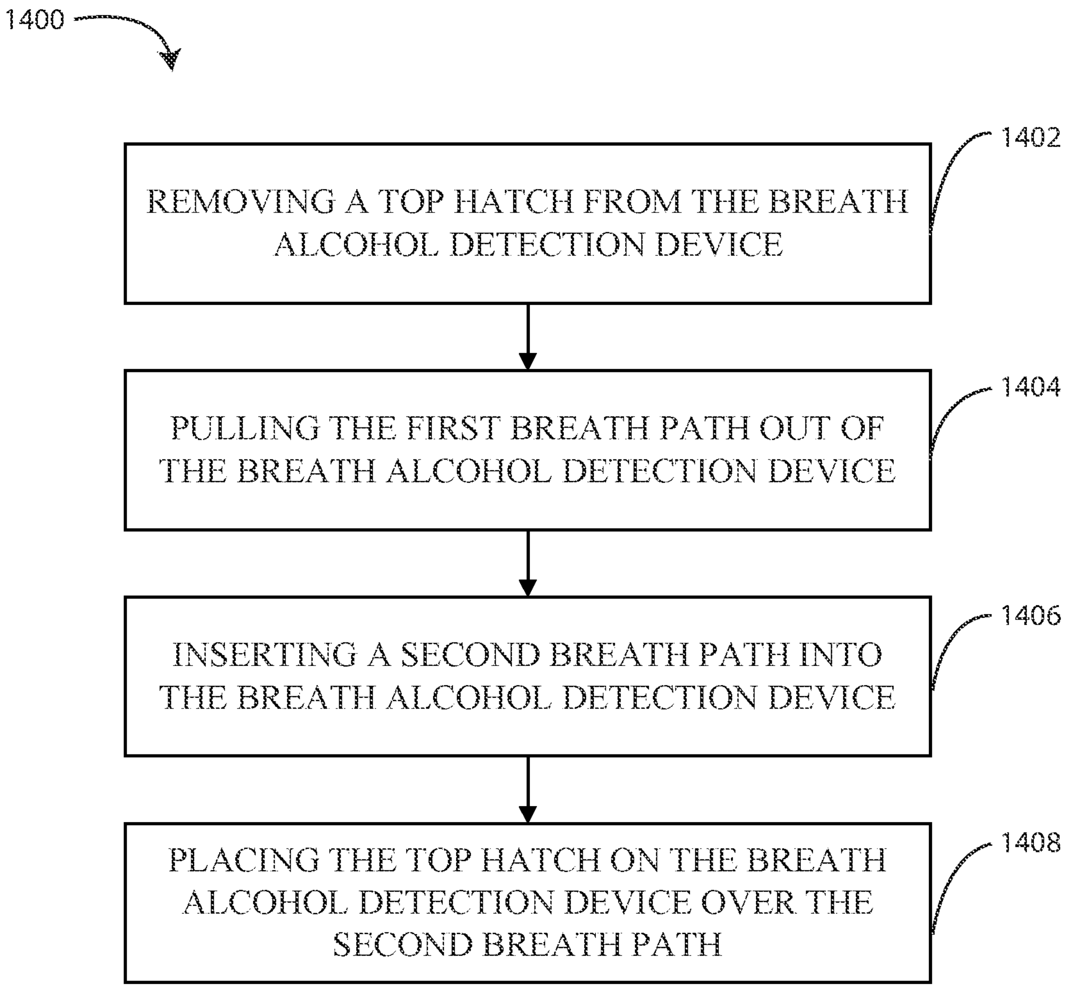
FIG. 14 is a method of replacing a breath path in a breath alcohol detection device in accordance with various embodiments herein.

Referring now to FIG. 14, a method of replacing a breath path in a breath alcohol detection device is shown in accordance with various embodiments herein. The method 1400 can include the step 1402 of removing a top hatch from the breath alcohol detection device. In some embodiments, the top hatch can be removably attached to the housing with a threaded fastener and step 1402 can include removing threaded fastener from a first side of the top hatch and pivoting the top hatch about the first side. Alternatively, the top hatch can be removably attached to the housing with a friction fit and step 1402 can include disengaging the friction fit between the top hatch and the breath alcohol detection device housing. In an embodiment, the method can further include removing a mouthpiece from the breath alcohol detection device prior to removing the top hatch from the breath alcohol detection device.

In some embodiments, the top hatch can be removed without the use of tools or with the use of readily available tools, such that the top hatch can be removed by any user of the alcohol detection device. Alternatively, the top hatch may only be removed with the use of specialized tools, such that only authorized users (such as technicians at a service center or repair center) are able to open the top hatch and access the internal components of the alcohol detection device.

The method 1400 can include the step 1404 of pulling the first breath path out of the breath alcohol detection device. The first breath can include a first breath path inlet, a first breath path outlet, and a first breath path port. In various embodiments, after removing the top hatch, the first breath path can be pulled out from a top hatch opening of the breath alcohol detection device. In an embodiment, the breath alcohol detection device can include a breath alcohol sensor having a first breath alcohol sensor port and step 1404 can further include disengaging the first breath path port from the first breath alcohol sensor port.

In an embodiment of the method, the first breath path comprises a breath path heater removably attached to the first breath path and the breath alcohol detection device further can include a first circuit board. Step 1404 can further include disengaging a plurality of breath path heater contact pads from a plurality of spring contacts disposed on the first circuit board upon removing the first breath path. Step 1404 can optionally include, after pulling the first breath path out of the breath alcohol detection device, removing the first breath path heater from the first breath path.

In some embodiments, the first breath path can be pulled out of the breath alcohol detection device without the use of tools or with the use of readily available tools, such that the breath path can be pulled out by any user of the breath alcohol detection device. Alternatively, the first breath path may only be removed with the use of specialized tools, such that only authorized users (such as technicians at a repair center) are able to pull out the first breath path from the alcohol detection device.

The method 1400 can include the step 1406 of inserting a second breath path into the breath alcohol detection device. The second breath path can also be referred to as a replacement breath path. The second breath path can include a second breath path inlet, a second breath path outlet, and a second breath path port. In an embodiment of the method, the second breath path port is configured to interface with the first breath alcohol sensor port, and step 1406 includes aligning the second breath path port with the first breath alcohol sensor port. In an embodiment of the method, the second breath path comprises a breath path heater removably attached to the second breath path and step 1406 can include attaching the second breath path heater to the second breath path and engaging a second plurality of breath path heater contact pads with the plurality of spring contacts disposed on the first circuit board.

The method 1400 can include the step 1408 of placing the top hatch on the breath alcohol detection device over the second breath path. In some embodiments, step 1408 may include compressing a gasket disposed on the second breath path inlet with the top hatch, such that the second breath path inlet forms a seal with the top hatch. In an embodiment of the method, the second breath path port is configured to interface with the first breath alcohol sensor port, and step 1408 includes compressing the second breath path port onto the first breath alcohol sensor port such that the second breath path port and the first breath alcohol sensor form a seal.

In various embodiments, the pressure applied to the breath path by the top hatch 110 causes breath path outlet gasket 205 to be pressed into a sealing engagement with the breath path outlet gasket sealing surface 1041.

In an embodiment, the method can further include placing a mouthpiece on the breath alcohol detection device after placing the top hatch onto the breath alcohol detection device.

Figure 15:
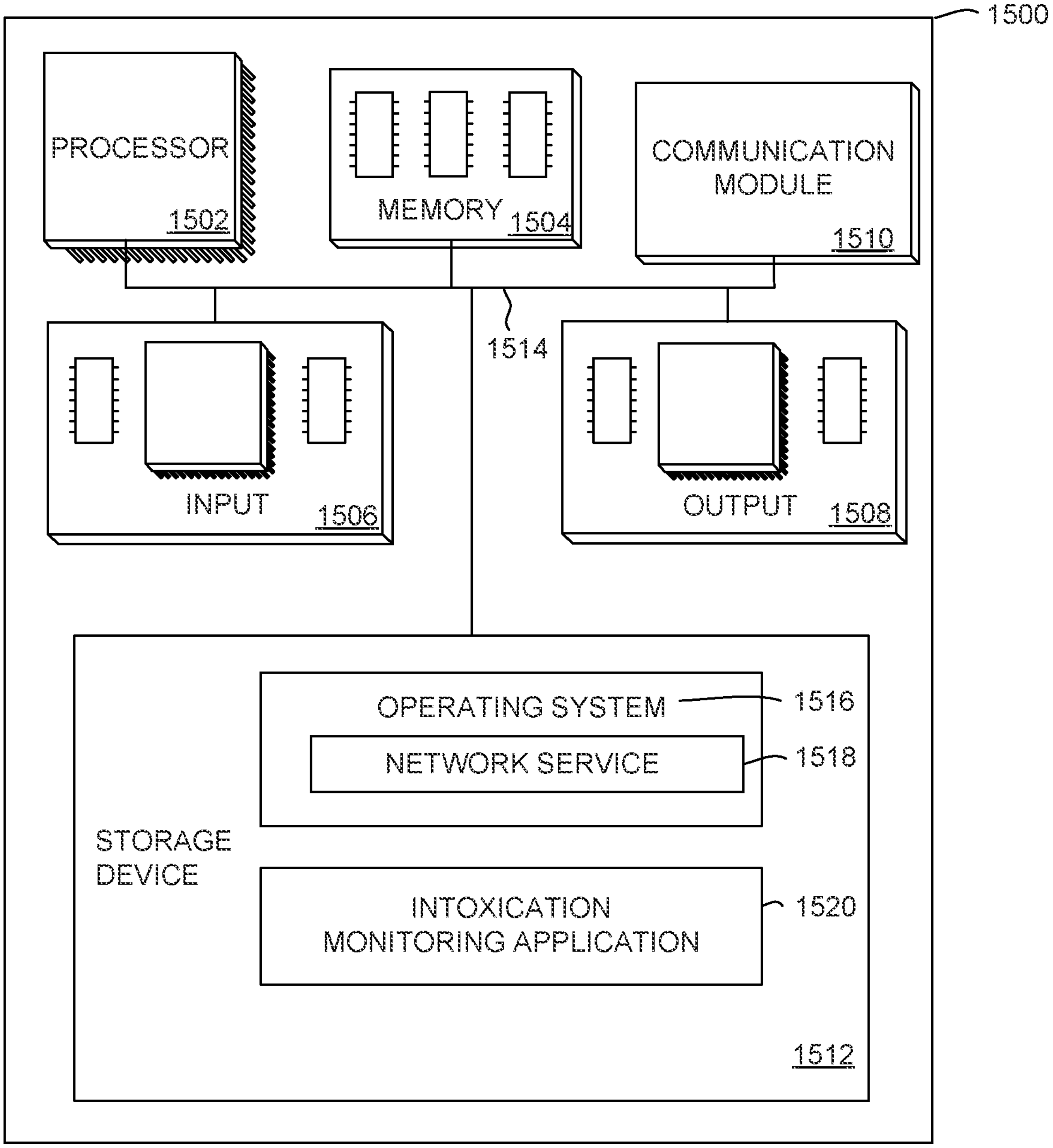
FIG. 15 is a computerized breath alcohol detection system in accordance with various embodiments herein.

Computer System (FIG. 15)

The systems and methods presented here may be implemented in part using a computerized device, such as a smartphone, handheld, or other computerized device. FIG. 15 shows a computerized breath alcohol detection system consistent with various examples described herein. FIG. 15 illustrates only one particular example of computing device 1500, and other computing devices 1500 may be used in other embodiments. Although computing device 1500 is shown as a standalone computing device, computing device 1500 may be any component or system that includes one or more processors or another suitable computing environment for executing software instructions in other examples and need not include all the elements shown here.

As shown in the specific example of FIG. 15, computing device 1500 includes one or more processors 1502, memory 1504, one or more input devices 1506, one or more output devices 1508, one or more communication modules 1510, and one or more storage devices 1512. Computing device 1500, in one example, further includes an operating system 1516 executable by computing device 1500. The operating system includes in various examples services such as a network service 1518. One or more applications, such as a breath alcohol detection application 1520, are also stored on storage device 1512 and are executable by computing device 1500.

Each of components 1502, 1504, 1506, 1508, 1510, and 1512 may be interconnected (physically, communicatively, and/or operatively) for inter-component communications, such as via one or more communication channels 1514. In some examples, communication channels 1514 include a system bus, network connection, inter-processor communication network, or any other channel for communicating data. Applications such as breath alcohol detection application 1520 and operating system 1516 may also communicate information with one another as well as with other components in computing device 1500.

Processors 1502, in one example, are configured to implement functionality and/or process instructions for execution within computing device 1500. For example, processors 1502 may be capable of processing instructions stored in storage device 1512 or memory 1504. Examples of processors 1502 include any one or more of a microprocessor, a controller, a digital signal processor (DSP), an application specific integrated circuit (ASIC), a field-programmable gate array (FPGA), or similar discrete or integrated logic circuitry.

One or more storage devices 1512 may be configured to store information within computing device 1500 during operation. Storage device 1512, in some examples, is known as a computer-readable storage medium. In some examples, storage device 1512 comprises temporary memory, meaning that a primary purpose of storage device 1512 is not long-term storage. Storage device 1512 in some examples includes a volatile memory, meaning that storage device 1512 does not maintain stored contents when computing device 1500 is turned off. In other examples, data is loaded from storage device 1512 into memory 1504 during operation. Examples of volatile memories include random access memories (RAM), dynamic random-access memories (DRAM), static random-access memories (SRAM), and other forms of volatile memories known in the art. In some examples, storage device 1512 is used to store program instructions for execution by processors 1502. Storage device 1512 and memory 1504, in various examples, are used by software or applications running on computing device 1500 such as intoxication interlock application 1520 to temporarily store information during program execution.

Storage device 1512, in some examples, includes one or more computer-readable storage media that may be configured to store larger amounts of information than volatile memory. Storage device 1512 may further be configured for long-term storage of information. In some examples, storage devices 1512 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories. Computing device 1500, in some examples, also includes one or more communication modules 1510. Computing device 1500 in one example uses communication module 1510 to communicate with external devices via one or more networks, such as one or more wireless networks. Communication module 1510 may be a network interface card, such as an Ethernet card, an optical transceiver, a radio frequency transceiver, or any other type of device that can send and/or receive information. Other examples of such network interfaces include Bluetooth, 3G, 4G, LTE, 5G, Wi-Fi radios, and Near-Field Communications (NFC), and Universal Serial Bus (USB). In some examples, computing device 1500 uses communication module 1510 to wirelessly communicate with an external device such as via public network such as the Internet.

Computing device 1500 also includes, in one example, one or more input devices 1506. Input device 1506, in some examples, is configured to receive input from a user through tactile, audio, or video input. Examples of input device 1506 include a touchscreen display, a mouse, a keyboard, a voice responsive system, video camera, microphone, or any other type of device for detecting input from a user.

One or more output devices 1508 may also be included in computing device 1500. Output device 1508, in some examples, is configured to provide output to a user using tactile, audio, or video stimuli. Output device 1508, in one example, includes a display, a sound card, a video graphics adapter card, or any other type of device for converting a signal into an appropriate form understandable to humans or machines. Additional examples of output device 1508 include a speaker, a light-emitting diode (LED) display, a liquid crystal display (LCD), or any other type of device that can generate output to a user.

Computing device 1500 may include operating system 1516. Operating system 1516, in some examples, controls the operation of components of computing device 1500, and provides an interface from various applications such intoxication interlock application 1520 to components of computing device 1500. For example, operating system 1516, in one example, facilitates the communication of various applications such as breath alcohol detection application 1520 with processors 1502, communication unit 1510, storage device 1512, input device 1506, and output device 1508. Applications such as intoxication interlock application 1520 may include program instructions and/or data that are executable by computing device 1500. As one example, breath alcohol detection application 1520 may include instructions that cause computing device 1500 to perform one or more of the operations and actions described in the examples presented herein.

Detection Unit Options

Throughout the application, a breath alcohol sensor has been described as a part of a breath alcohol detection device. The breath alcohol sensor has sometimes been described as a fuel cell detector element. In alternative methods and systems, other types of sensors or detection elements can be used.

For example, instead of or in addition to a fuel cell detection element, the system can include one or more of a complementary metal oxide semiconductor (CMOS) sensor, a metal oxide semiconductor (MOS) sensor, a semiconductor sensor, and an infrared (IR) sensor.

In some examples, detection elements can be used that provide a continuous signal. Detection elements for alcohol that can provide a continuous signal are a complementary metal oxide semiconductor (CMOS) sensor, a metal oxide semiconductor (MOS) sensor, a semiconductor sensor, and an infrared (IR) sensor. These detection elements and detection elements that provide a continuous signal do not need to wait for a predetermined time period after receiving a gas sample to provide a gas alcohol content reading that is considered accurate. In contrast, fuel cell detection elements operate on a fixed volume gas sample when measuring alcohol content.

In other examples, instead of testing a user's breath for alcohol, the detection unit can test the user's breath for *cannabis*, opioids, or other intoxicants. In other examples, instead of testing the user's breath for an intoxicant, the detection unit can be a transdermal device that is in contact with the user's skin and detects a level of alcohol, *cannabis*, opioids, or other intoxicants in a user. Transdermal sensors can be part of a wrist-worn device, an ankle-worn device, a device attached to another part of the user's body, or a device embedded in a steering wheel or another part of the vehicle. If a transdermal unit is used as the detection unit, then instead of prompting the user to provide a breath sample, the system can ask the user to bring the detection unit into contact with the user's skin. If the detection unit is already in contact with the user's skin, then the system can simply take the measurement and determine if there is an intoxicant present above a threshold.

These alternatives for a detection unit and a detection element can be used with each of the systems described herein instead of the breath detection element that is otherwise described.

The systems and methods presented here may be implemented in part using a computerized device, such as a smartphone, handheld, or other computerized device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed, and arranged, constructed, manufactured, and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A breath alcohol detection device comprising:

a housing;

a first circuit board disposed within the housing, the first circuit board comprising one or more compressible contacts electrically connected to the first circuit board;

a breath path, the breath path comprising:

a breath path inlet, a breath path outlet, a first bend disposed between the breath path inlet and the breath path outlet, a second bend disposed between the first bend and the breath path outlet, and an elongate portion disposed between the second bend and the breath path outlet; and a breath path heater, wherein the breath path heater is configured to wrap around an outside portion of the breath path, the breath path heater comprising a plurality of breath path heater contact pads electrically connected to the breath path heater;

wherein the breath path is configured to fit within the housing; and wherein the breath alcohol detection device is configured so that insertion of the breath path into the housing causes compression of the one or more compressible contacts by the breath path heater contact pads and forms an electrical connection between the breath path heater and first circuit board.

2. The breath alcohol detection device of claim 1, the breath path heater comprising:

a first heater portion comprising a first resistive heating element, a second heater portion comprising a second resistive heating element, and a connecting portion joining the first heater portion and second heater portion.

3. The breath alcohol detection device of claim 2, wherein the connecting portion does not include a heating element.

4. The breath alcohol detection device of claim 2, wherein the first resistive heating element and second resistive heating element are in series and are controlled together.

5. The breath alcohol detection device of claim 2, wherein the first resistive heating element and second resistive heating element are controlled independently.

6. The breath alcohol detection device of claim 1, the breath path further comprising:

a first surface comprising a first breath path attachment structure;

a second surface comprising a second breath path attachment structure.

7. The breath alcohol detection device of claim 6, the breath path heater further comprising:

a first resistive heating element; and a first heater attachment structure configured to removably attach to the first breath path attachment structure;

a second heater portion comprising:

a second resistive heating element; and a second heater attachment structure configured to removably attach to the second breath path attachment structure; and a connecting portion joining the first heater portion and second heater portion.

* * * * *